(12) United States Patent
Zheng et al.

(10) Patent No.: US 9,044,451 B2
(45) Date of Patent: Jun. 2, 2015

(54) USE OF DELTA TOCOPHEROL FOR THE TREATMENT OF LYSOSOMAL STORAGE DISORDERS

(75) Inventors: Wei Zheng, Potomac, MD (US); Juan Jose Marugan, Gaithersburg, MD (US); Ke Liu, Cambridge, MD (US); Noel Terrence Southall, Chevy Chase, MD (US); Christopher P Austin, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 69 days.

(21) Appl. No.: 13/810,774

(22) PCT Filed: Jul. 19, 2011

(86) PCT No.: PCT/US2011/044590
§ 371 (c)(1),
(2), (4) Date: Jan. 17, 2013

(87) PCT Pub. No.: WO2012/012473
PCT Pub. Date: Jan. 26, 2012

(65) Prior Publication Data
US 2013/0123214 A1 May 16, 2013

Related U.S. Application Data

(60) Provisional application No. 61/365,712, filed on Jul. 19, 2010.

(51) Int. Cl.
| | | |
|---|---|---|
| A61K 31/355 | (2006.01) | |
| A61K 31/724 | (2006.01) | |
| A61K 45/06 | (2006.01) | |
| A61K 31/36 | (2006.01) | |
| A61K 31/496 | (2006.01) | |
| A61K 36/185 | (2006.01) | |

(52) U.S. Cl.
CPC ............... *A61K 31/355* (2013.01); *A61K 31/36* (2013.01); *A61K 31/496* (2013.01); *A61K 31/724* (2013.01); *A61K 36/185* (2013.01); *A61K 45/06* (2013.01)

(58) Field of Classification Search
CPC ... A61K 31/355; A61K 45/06; A61K 31/724; A61K 31/36; A61K 2300/00
USPC .................................................. 514/458, 58
See application file for complete search history.

(56) References Cited

PUBLICATIONS

Valenzuela et al. Differential Inhibitory Effect of alpha-, beta-, gamma-, and delta-Tocopherols on the Metal-Induced Oxidation of Cholesterol in Unilamellar Phospholipid-Cholesterol liposomes. J Food Sci 67:2051-2055, 2002.*
Sontag et al. Influence of major structural features of tocopherols and tocotrienols on their w-oxidation by tocopherol-w-hydroxylase. J Lipid Res 48:1090-1098, 2007.*
Liu et al. Reversal of defective lysosomal transport in NPC disease ameliorates liver dysfunction and neurodegeneration in the npc1-/- mouse. Proc Natl Acad Sci 106:2377-2382, 2009.*
Solgar Natural Liquid Vitamin E. http://www.iherb.com/Solgar-Natural-Liquid-Vitamin-E-4-fl-oz-118-4-ml/9742 Accedded on Jul. 28, 2014.*
Bascunan-Castillo et al. (2004) J. Appl. Genet. 45(4):461-467 "Tamoxifen and vitamin E treatments delay symptoms in the mouse model of Niemann-Pick C."
Helquist et al. (2009) Drugs of the Future 34(4):315-331 "Current Status of Drug Therapy Development for Niemann-Pick Type C Disease."
International Search Report and Written Opinion issued Dec. 1, 2011 in PCT/US2011/044590.
Narushima et al. (2008) Mol. Pharmacol. 74(1):42-49 "Niemann-Pick C1-Like 1 Mediates α-Tocopherol Transport."
Platt et al. (2009) Biochimica et Biophysica Acta 1793(4):737-745 "Treating lysosomal storage disorders: Current practice and future prospects."
Sontag et al. (2002) The Journal of Biological Chemistry 277(28):25290-25296 "Cytochrome P450 ω-Hydroxylase Pathway of Tocopherol Catabolism."
Tucker et al. (2005) Biomedicine & Pharmacotherapy 59(7):380-387 "Alpha-tocopherol: roles in prevention and therapy of human disease."
Björkhem (2013) Curr. Opin. Lipidol 24:283-287 "Cerebrotendinous xanthomatosis."
Eng et al. (2006) Genet. Med. 8(9):539-548 "Fabry disease: Guidelines for the evaluation and management of multi-organ system involvement."
Gullotta et al. (1996) Neuropediatrics 27:37-41 "Differentiation of Rare Leukodystrophies by Post-Mortem Morphological and Biochemical Studies: Female Adrenoleuko-dystrophy-Like Disease and Late-Onset Krabbe Disease."
Jabs et al. (2008) Journal of Neurochemistry 106:1415-1425 "Accumulation of bis (monoacylglycero) phosphate and gangliosides in mouse models of neuronal ceroid lipofuscinosis."

(Continued)

*Primary Examiner* — Brandon Fetterolf
*Assistant Examiner* — Yih-Horng Shiao
(74) *Attorney, Agent, or Firm* — Swanson & Bratschun, L.L.C.

(57) ABSTRACT

This disclosure relates generally to the treatment of lysosomal storage disorders. Specifically, the disclosure relates to a novel use of delta tocopherol in the treatment of diseases and conditions related to lysosomal storage disorders. Included in the present disclosure is a method for the modulation of cholesterol recycling. Further, the disclosure relates to conditions such as Niemann-Pick type C disease, Farber disease, Niemann-Pick type A disease, Wolman disease and Tay Sachs disease. Further included in the present disclosure is a method for treating lysosomal storage disorders comprising the administration of delta tocopherol. Further included in the present disclosure is a method for treating lysosomal storage disorders comprising the administration of delta tocopherol in combination with cyclodextrin to a patient in need thereof.

18 Claims, 29 Drawing Sheets

(56) References Cited

PUBLICATIONS

Marschner et al. (2011) Science 333:87-90 "A Key Enzyme in the Biogenesis of Lysosomes Is a Protease That Regulates Cholesterol Metabolism."

McGlynn et al. (2004) The Journal of Comparative Neurology 480:415-426 "Differential Subcellular Localization of Cholesterol, Gangliosides, and Glycosaminoglycans in Murine Models of Mucopolysaccharide Storage Disorders."

Micsenyi et al. (2009) J. Neuropathol. Exp. Neurol. 68(2):125-135 "Neuropathology of the $Mcoln1^{-/-}$ Knockout Mouse Model of Mucolipidosis Type IV."

Sandhoff (2013) Biochemical Society Transaction 41(6): 1562-1568 "Metabolic and cellular bases of sphingolipidoses."

Silence (2013) Molecular Genetics and Metabolism 109:194-200 "Glucosylceramide modulates endolysosomal pH in Gaucher disease."

Valenzuela et al. (2003) Biol. Res. 36:291-302 "Cholesterol oxidation: Health hazard and the role of antioxidants in prevention."

Walkley et al. (2005) Neuropathology and Applied Neurobiology 31:536-544 "Abnormal neuronal metabolism and storage in mucopolysaccharidosis type VI (Maroteaux-Lamy) disease."

Yamashita et al. (1992) The Journal of Nutrition 2440-2446 "Sesame Seed Lignans and γ-Tocopherol Act Synergistically to Produce Vitamin E Activity in Rats."

Yates et al. (1983) Neurochemical Pathology 1:103-123 "Sudanophilic Leukodystrophy with Large Amounts of Cholesterol Ester."

* cited by examiner

Filipin (Blue)
Cell Mask (Red)

Lysotracker (Red)
Hoescht (Blue)

α-tocopherol, $R_1 = R_2 = R_3 = CH_3$     γ-tocopherol, $R_1 = R_2 = CH_3 R_3 = H$
α-tocotrienol, $R_1 = R_2 = R_3 = CH_3$    γ-tocotrienol, $R_1 = R_2 = CH_3 R_3 = H$ β-tocopherol, $R_1 = R_3 = CH_3; R_2 = H$  δ-tocopherol, $R_1 = R_2 = R_3 = H$
β-tocotrienol, $R_1 = R_3 = CH_3; R_2 = H$ δ-tocotrienol, $R_1 = R_2 = R_3 = H$ 4 Days Treatment - WT and NPA

WT

NPA

4 Days Treatment – WT and Wolman6144

WT

No Treat     δ-toc-40uM     α-toc-80uM     MBCD-300uM

Wolman6144

No Treat     δ-toc-40uM     α-toc-80uM     MBCD-300uM

4 Days Treatment - WT and Wolman11851

WT

No Treat     $\delta$-toc-40uM     $\alpha$-toc-80uM     MBCD-300uM

Wolman11851

No Treat     $\delta$-toc-40uM     $\alpha$-toc-80uM     MBCD-300uM

4 Days Treatment – WT and Tay Sachs

WT

No Treat     δ-toc-40uM     α-toc-80uM     MBCD-300uM

Tay Sachs

No Treat     δ-toc-40uM     α-toc-80uM     MBCD-300uM

4 Days Treatment – WT and Farber

WT

No Treat     δ-toc-40uM     α-toc-80uM     MBCD-300uM

Farber

No Treat     δ-toc-40uM     α-toc-80uM     MBCD-300uM

4 Days Treatment - WT and Wolman6144

WT

No Treat     δ-toc-40uM     α-toc-80uM     MBCD-300uM

Wolman6144

No Treat     δ-toc-40uM     α-toc-80uM     MBCD-300uM

4 Days Treatment - WT

Total Lipids Including Phospholipids

No Treat    δ-toc-40uM    α-toc-80uM

Neutral Lipids (CE/Triglycerides)

No Treat    δ-toc-40uM    α-toc-80uM

4 Days Treatment - Farber

Total Lipids Including Phospholipids

No Treat      δ-toc-40uM      α-toc-80uM

Neutral Lipids (CE/Triglycerides)

No Treat      δ-toc-40uM      α-toc-80uM

4 Days Treatment - NPA

Total Lipids Including Phospholipids

No Treat          δ-toc-40uM          α-toc-80uM

Neutral Lipids (CE/Triglycerides)

No Treat          δ-toc-40uM          α-toc-80uM

4 Days Treatment - Wolman6144

Total Lipids Including Phospholipids

No Treat        $\delta$-toc-40uM        $\alpha$-toc-80uM

Neutral Lipids (CE/Triglycerides)

No Treat        $\delta$-toc-40uM        $\alpha$-toc-80uM

4 Days Treatment – Wolman11851

Total Lipids Including Phospholipids

No Treat        δ-toc-40uM        α-toc-80uM

Neutral Lipids (CE/Triglycerides)

No Treat        δ-toc-40uM        α-toc-80uM

4 Days Treatment - Tay Sachs

Total Lipids Including Phospholipids

No Treat        δ-toc-40uM        α-toc-80uM

Neutral Lipids (CE/Triglycerides)

No Treat        δ-toc-40uM        α-toc-80uM

USE OF DELTA TOCOPHEROL FOR THE TREATMENT OF LYSOSOMAL STORAGE DISORDERS

RELATED APPLICATIONS

The present application is a national phase entry filed pursuant to 35 USC §371 of International Patent Application No. PCT/US2011/044,590, filed Jul. 19, 2011, which application claims priority to U.S. Provisional Patent Application No. 61/365,712, filed Jul. 19, 2010; each of the foregoing applications is incorporated herein by reference in its entirety.

STATEMENT OF GOVERNMENT INTEREST

The instant application was made with government support; the government has certain rights in this invention.

TECHNICAL FIELD

This disclosure relates generally to the treatment of lysosomal storage disorders. Specifically, the disclosure relates to a novel use of delta tocopherol in the treatment of diseases and conditions related to lysosomal storage disorders. Included in the present disclosure is a method for the modulation of cholesterol recycling. Further, the disclosure relates to conditions such as Niemann-Pick type C disease, Farber disease, Niemann-Pick type A disease, Wolman disease and Tay Sachs disease. Further included in the present disclosure is a method for treating lysosomal storage disorders comprising the use of δ-tocopherol. Further included in the present disclosure is a method for treating lysosomal storage disorders comprising the use of δ-tocopherol in combination with cyclodextrin.

BACKGROUND

Tocopherols are natural products widely used as vitamin E for human health, cosmetic ingredients and food antioxidants. The main source of tocopherols is the deodorized distillate produced by the manufacture process of edible oil. The main constituents of the tocopherols extracted from deodorized distillate are α, β, γ, and δ-tocopherols. Their molecular structures have a common core ring, differing only in the number of attached methyl groups. Although the structures are quite similar, it is known in the art that α-tocopherol has the highest biopotency among all the isomeric forms. Current research involving tocopherols is focused on α-tocopherol, emphasizing α-tocopherol's use as an antioxidant.

In normal physiological cell function, lysosomal enzymes break down macromolecules in cells. Normal metabolism allows the cells to remove expended metabolites. Defects or deficiencies of lysosomal enzymes or other lysosomal components can result in the accumulation of undegraded metabolites. These defects or deficiencies result in Lysosomal Storage Disorders (LSDs).

Cholesterol is an essential component of the cell membrane and plays an important role in maintaining integrity and fluidity of the cell membrane with additional lipids. The appropriate proportion and makeup of cholesterol in the cell membrane is important for regulation of cell signaling, receptor function, ion permeability and endocytosis. In addition, cholesterol is the precursor molecule for synthesis of bile acids, Vitamin D and steroid hormones. Cholesterol concentration is regulated on two levels; in the body as a whole and intracellularly. Cholesterol is primarily synthesized in cells and transported in blood by lipid binding proteins. While the mechanisms of cholesterol transport in blood and cholesterol synthesis in cells are well characterized, the many details of free cholesterol trafficking in cells remain unclear. Cholesterol enters cells through low-density lipoprotein (LDL) receptors via endocytosis or cholesterol is de novo synthesized inside cells. The internalized cholesterol esters are hydrolyzed by acid lipase to form free cholesterols in late endosomes/lysosomes that are delivered to NPC1 and NPC2 proteins for further processing. Cholesterol may be transported to other proteins and/or to membrane microdomains such as lipid rafts and other vesicles. It is known that most of these free cholesterols recycle back to cell membrane; some of them efflux out of cells, and some of them move to ER for storage after esterification.

Lysosomal storage diseases (lysosomal storage disorders) are a group of ~50 diseases with a common feature of lysosomal accumulation of macromolecules such as lipids or glycoproteins in patient cells. The diseases are caused by inherited genetic mutations that result in deficiency of lysosomal enzyme or protein. Once the hydrolysis or transport of macromolecules such as lipids and glycoproteins is reduced by a mutation of an enzyme or protein in lysosome, they are accumulated which causes the enlargement of lysososomes as well as malfunction of lipids recycling and utilization in cells. Degeneration or death of affected cells occurs in certain tissues which are varied in different lysosomal storage diseases. The hepatosplenomegaly and neuronal degeneration are common features of many lysosomal storage diseases.

One identified LSD is Niemann-Pick type C disease (NPCD), an autosomal recessive disease with an estimated incidence of 1:150,000. This disease is characterized by a lysosomal accumulation of unesterified cholesterol and other lipids in many cell types, probably due to impairment of the retrograde transport of lipids from the late endosomes and/or lysosomes to the plasma membrane or endoplasmic reticulum (ER). The clinical manifestation includes hepatosplenomegaly, vertical gaze palsy, and progressive neurodegeneration characterized by cerebellar ataxia, bulbar dysfunction, and variable degrees of cognitive decline. Most often, the onset of symptoms occurs in early childhood, leading to death within a decade. Two human genes have been identified for NPCD: mutations in NPC1 are causative in nearly 95% of all NPC cases, while mutations in NPC2 account for the rest. Over 230 mutations have been identified in the NPC1 gene, nearly ⅔ of which are missense mutations. NPC1 is a highly-conserved integral membrane protein with 13 transmembrane domains, while the NPC2 gene encodes a small soluble protein. Both proteins are located in late endosomes and lysosomes. Recent structure and biochemical studies have revealed that NPC1 and NPC2 bind to cholesterol in opposite orientations, leading to a working model of these two proteins: NPC2 captures the cholesterol liberated from LDL, and then transfers it to the NPC1 on the membrane for subsequent trafficking out of the lysosomes. In NPCD patients, the cholesterol trafficking out of late endosomes and lysosomes is blocked resulting in an accumulation of free cholesterols in late endosomes and lysosomes. This accumulation of cholesterol eventually affects the lysosomal homeostasis, triggering also the accumulation of other lysosomal substrates such us glycosphingolipids. Moreover, glycosphingolipids accumulation in sphingolipid storage diseases (SLSD) as result of a defective lysosomal hydrolase or activator protein also affects cholesterol homeostasis elevating cellular cholesterol levels.

Currently, there is no cure for NPCD and all established therapies are for relief of symptoms with limited efficacy. Clinical trials with Miglustat (N-butyldeoxynojirimycin, Zavesca®) are in progress with favorable preliminary results. Miglustat is an iminosugar that inhibits glucosylceramide synthase, an enzyme responsible for a series of reactions that lead to the synthesis of most glycosphingolipids (GSL). This drug crosses the blood-brain barrier, reduces the substrate availability for synthesizing GSL, and thus reduces GSL accumulation in the brain. This substrate reduction effect seems to relieve the symptoms in NPC patients. Recently, several other compounds including allopregnanolone, T0901317, curcumin and cyclodextrin have also been reported to have beneficial effects on NPC cell or animal models. The full therapeutic benefits of these drugs still need to be evaluated. Despite these studies, an effective treatment for NPC patients is still an unmet medical need.

Recent advances in technologies for high-throughput screening (HTS) have made it possible to screen the cell-based NPC disease model against compound libraries to identify lead compounds for the new drug development. Two such attempts have been made which applied the filipin cholesterol staining assay in NPC patient-derived skin fibroblasts. Though some active compounds were reported from these screens, none of them are useful for the further drug development. In addition, the drug development process usually takes an average of 8-12 years costing on the order of hundreds of millions of dollars. The failure rate of drug development is very high due to unpredictable compound toxicity in human and disproportional efficacy between human and model systems. The present invention is directed toward overcoming the problems discussed above.

SUMMARY OF THE EMBODIMENTS

We identify, in one embodiment, the use of δ-tocopherol for the treatment of LSDs. Further, we identify the use of δ-tocopherol in reducing the accumulation of free cholesterols. Additionally we teach the use of δ-tocopherol for the reduction of the size of enlarged lysosomes.

In one embodiment, we disclose a method for treating lysosomal storage disorder comprising administering to a patient in need thereof a pharmaceutically effective amount of a δ tocopherol. In one embodiment, we disclose a pharmaceutically effective amount of δ tocopherol of 50 uM plasma and/or tissue concentration. In one embodiment, we disclose a pharmaceutically effective amount of δ tocopherol of less than 50 uM. In one embodiment, we disclose a pharmaceutically effective amount of δ tocopherol of less than 40 uM. In one embodiment, we disclose a pharmaceutically effective amount of δ tocopherol of less than 30 uM. In one embodiment, we disclose a pharmaceutically effective amount of δ tocopherol of less than 20 uM. In one embodiment, we disclose a pharmaceutically effective amount of δ tocopherol of less than 15 uM. In one embodiment, we disclose a pharmaceutically effective amount of δ tocopherol of less than 10 uM. In one embodiment, we disclose a pharmaceutically effective amount of δ tocopherol of less than 7.8 uM. In one embodiment, we disclose a pharmaceutically effective amount of δ tocopherol without significant cytotoxicity.

The disclosure further provides a method for treating a mammal having a lysosomal storage disorder by administering a pharmaceutical composition comprising a dosage of a δ-tocopherol effective to treat the lysosomal storage disorder; and a beta-cyclodextrin compound, in which the dosage of the δ-tocopherol compound is less than about 1000 IU/kg per day. In particular embodiments, the dosage of δ-tocopherol is less than 500 IU/kg per day, less than 50 IU/kg per day, less than 5 IU/kg per day, or less than 0.5 IU/kg per day. In one embodiment of the methods of treatment, the disclosure provides a method for treating a mammal having a lysosomal storage disorder by administering a pharmaceutical compo-sition comprising a dosage of a δ-tocopherol compound, wherein the dosage of the δ-tocopherol compound is less than an accepted dose of α-tocopherol. In one embodiment of the methods of treatment, the disclosure provides a method for treating a mammal having a lysosomal storage disorder by administering a pharmaceutical composition comprising a dosage of a δ-tocopherol compound, wherein the dosage of the δ-tocopherol is less than about 1000 IU/kg per day. In particular embodiments, the dosage of δ-tocopherol is less than 500 IU/kg per day, less than 50 IU/kg per day, less than 5 IU/kg per day, or less than 0.5 IU/kg per day.

We further disclose the treatment with δ-tocopherol, wherein the lysosomal storage disorder is selected from the group consisting of Niemann-Pick Disease, Mucopolysac-charidoses disorder, and Neuronal Ceroid Lipofuscinoses. We further disclose the treatment with δ-tocopherol, wherein the lysosomal storage disorder is selected from the group consisting of Niemann-Pick type C disease, Farber disease, Niemann-Pick type A disease, Wolman disease and Tay Sachs disease. In one embodiment, the composition of δ tocopherol excludes α, β, and γ tocopherol for the treatment of LDS. In one embodiment, the composition of δ-tocopherol excludes α, β, and γ tocopherol for the treatment of NPCD. In one embodiment the composition of δ tocopherol excludes any one of α, β, and γ tocopherols, and/or any combination thereof, for the treatment of LDS. In one embodiment, the composition of δ tocopherol comprises cyclodextrin for the treatment of LDS. In one embodiment the composition of δ tocopherol excludes any one of α, β, and γ tocopherols, and/or any combination thereof, for the treatment of LDS, and comprises cyclodextrin for the treatment of LDS. In one embodiment, the composition of δ-tocopherol excludes α, β, and γ tocopherol for the treatment of NPCD. We disclose a method for reducing cholesterol accumulation in cells comprising administering a composition of δ tocopherol. We further disclose a method for reducing cholesterol accumulation in cells comprising administering a composition of δ tocopherol which excludes any one of α, β, and γ tocopherol or combinations thereof. We further disclose a method for treatment of a disease characterized by increased cholesterol accumulation wherein the cholesterol accumulation in cells is reduced by a method comprising administering a composition of δ tocopherol which excludes any one of α, β, and γ tocopherol or combinations thereof to a patient in need.

Figure 1A:
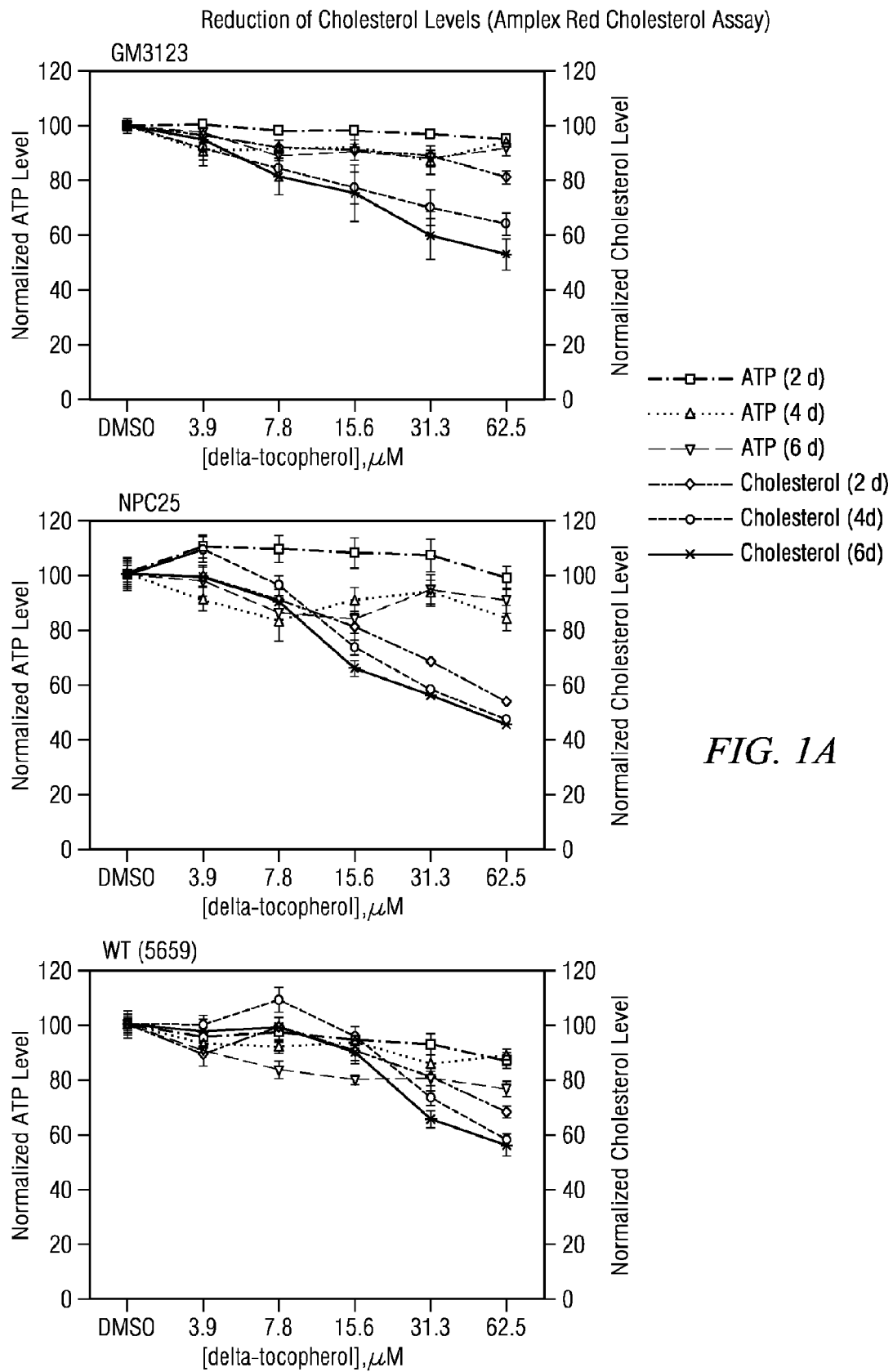
FIG. 1. A) The influence of delta-tocopherol on free cholesterol (green lines, right y-axis) and ATP level (red lines, left y-axis) in WT and NPC fibroblasts. On day 0 cells were seeded in 1536-well plates. On day 1, 3, or 5, delta-tocopherol dissolved in DMSO was added to the cells at various final concentrations as indicated in the figure. On day 7, the cells were examined for free cholesterol and ATP levels by Amplex Red cholesterol assay and ATP-lite assay, respectively. Free cholesterol and ATP levels of δ-tocopherol treated cells were normalized against those of DMSO treated cells of the same type and expressed as the percentage of DMSO treated cells. Error bars represented standard error of n=8 values. B) Filipin staining of the NPC cells treated with δ-tocopherol. On day 0, cells were seeded on black clear-bottom 96-well plates at 500 cells/well. On day 1, culture medium was replaced with medium containing different concentrations of δ-tocopherol or matching DMSO. On day 4, media were replaced again with ones containing fresh compounds. On day 6, filipin staining (blue) as well as CellMask staining (red) was performed as described in the method section. C) Lysotracker staining of the NPC cells treated with δ-tocopherol. Cells were treated similarly as in FIG. 1B and stained by Lysotracker Red and Hoechst as described in the method session.

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

DETAILED DESCRIPTION

We disclose δ-tocopherol for the treatment of LSDs. Surprisingly, δ-tocopherol is the most potent of the eight isoforms of vitamin E for the reduction of cholesterol accumulation in NPCD fibroblasts. We disclose a potency with delta tocopherol 6 to 8 times higher than with α-, β- and γ-tocopherols ($EC_{50}$ values between 60-80 μM). It has been reported that in human plasma α-tocopherol is the most abundant vitamin E vitamin with a concentration in the range of 26 uM. The concentrations for β- and γ-tocopherols are much less (~1-3 μM) whereas the plasma concentration for δ-tocopherol is the lowest at the tracer value (~0.1 μM). We disclose δ-tocopherol for the treatment of LSDs. δ-tocopherol has a low physiological concentration in the body and is significantly potent in reduction of cholesterol accumulation.

Vitamin E, as disclosed in the art, generally refers to α tocopherol; however, other vitamers or isoforms exist, which include α-, β-, γ- and δ-isoforms. The differences in α-, β-, γ- and δ-isoforms relies on the position and number of methyl groups on the phenol ring, in addition to the corresponding tocotrienols having three double bonds in the side chain. The function of vitamin E is thought to be through its antioxidant effects in cell membrane by reducing free radicals critical for the structural integrity of cells. As a lipid-soluble molecule, vitamin E is believed to insert into the cell membrane for its function. The plasma concentration of vitamin E is one per 2000-3000 lipids and is easily depleted if it is not regenerated or is deficient in diet. The deficiency of vitamin E presents symptoms primarily in neuronal system including ataxia, dysarthria, hyporeflexia and reduced vibration sense as well as cardiomyopathy and retinitis pigmentosa. On other hand, high doses of vitamin E have been used and propose for the treatment of neurological disorders. The potential link of vitamin E deficiency with cancer and inflammation has been reported with regard to the antioxidant scavenging activity of vitamin E.

Lysosomal storage diseases include many disorders such as mucopolysaccharidosis, mucolipidosis, spingolipidosis, GM2 gangliosidosis, GM2 activator protein deficiency, Niemann-Pick disease, Gaucher's disease, Fabry's disease, Farber's disease, Metachromatic leukodystrophy, mucosulfatidosis, Krabbe's disease, Sphingolipid activator protein deficiencies, Lysosomal acid lipase deficiency, Wolman's disease, Cholesterol ester storage disease, Cerebrotendious xanthomatosis, Neuronal ceroid lipofuscinosis, oligosaccharidosis and related disorders, and lysosomal transport defects.

Blood cholesterol level of cholesterol is well regulated wherein ~70% cholesterol is synthesized by the body and ~30% of it is absorbed/reabsorbed from the intestine. Cholesterol is a vital structural component in cell membrane, as cellular cholesterol homeostasis is important to maintain a variety of cellular functions. Cholesterol is usually bound to lipid binding proteins in blood and delivered to cells by LDL. The endocytosis formed coated vesicles containing LDL reach the late endosome/lysosme and the free cholesterols are released from LDL by acid lipase. The free cholesterol is then delivered to NPC2 and NPC1 proteins located in late endosome/lysosme. Free cholesterol is then moved to the trans-golgi network (TNG) for efflux through cell membrane and/ or to ER for esterification for normal intracellular cholesterol storage. Mutations in NPC1/2 proteins result in the malfunction in this cholesterol trafficking pathway in cells with the consequence of free cholesterol accumulation in late endosome/lysosme. This cholesterol recycling malfunction subsequently results in the accumulation of other membrane lipids in the NPC cells. In addition, it is well known that cholesterol and sphingolipids accumulation induce oxidative stress. Thus, in the case of NPC oxysterols accumulation has been link with the apoptotic triggering. In brain, loss of Purkinje neurons in the cerebellar cortex due to neuronal degeneration is most predominant in NPCD. Purkinje neurons rely on the cholesterols synthesized in astrocytes which are delivered to them. Deficiency in NPC1 or NPC2 proteins may block the cholesterol movement from late endosome/lysosme to other compartments in cells which impairs the critical lipid recycling/movement (including many other lipids) and eventually results in cell death. We disclose a correction of cholesterol movement malfunction in NPC cells with an activation/enhancement of an alternative cholesterol recycling pathway as a new therapeutic strategy to treat the deadly NPCD. In addition, the antioxidative effect of δ-tocopherol should have an impact in reducing the oxysterols levels and therefore decreasing the apoptotic signal as part of the overall proposed NPC treatment. Similar effects in reducing the oxidative stress observed in other LSD should being considered.

We disclose tocopherols in NPC cells as well as in other LSD cells. In normal conditions, cholesterol recycling/movement in the membrane mainly relies on the NPC1/NPC2 protein dependent pathway. The cholesterol influx and efflux is balanced maintaining normal cellular functions. These functions include the rapid endocytic/exocytic processes and lipid movement/recycling in the membrane system. The continuous lipid movements in the plasma membrane and in intracellular compartments are critical for maintaining the proper functions of cellular signaling pathways. After the treatment with δ-tocopherols inserted into the membranes, including the plasma membrane as well as the membranes in intracellular organelles, the membrane lipid movement is slightly enhanced accounting for the slight reduction of free cholesterol in wild type cells caused by an increase in cholesterol efflux. The resultant reduction in cholesterol esters is probably due to the increasing need for free cholesterol. In NPC cells, the mutations in NPC1 and NPC2 proteins result in the cessation of cholesterol movement in the membrane system as well as the other lipids. The cholesterol efflux is significantly reduced and free cholesterol accumulates in lysosome. With δ-tocopherol treatment, the accumulated free cholesterols in late endodome/lysosome are reduced which are mediated by an alternative NPC1/NPC2-independent pathway. This alternative lipid movement pathway is stimulated/enhanced by insertion of δ-tocopherols into the membrane that led to an increase in cholesterol efflux. Cholesterol efflux via lipid rafts and/or other vesicle are candidates for this alternative lipid movement pathway. This model explains the effect of δ-tocopherols on the reduction of enlarged lysosome size in four types of LSDs as the enhanced lipid movement may clean the accumulated lipids in late endosome and lysosome.

Figures 1B, 1C:
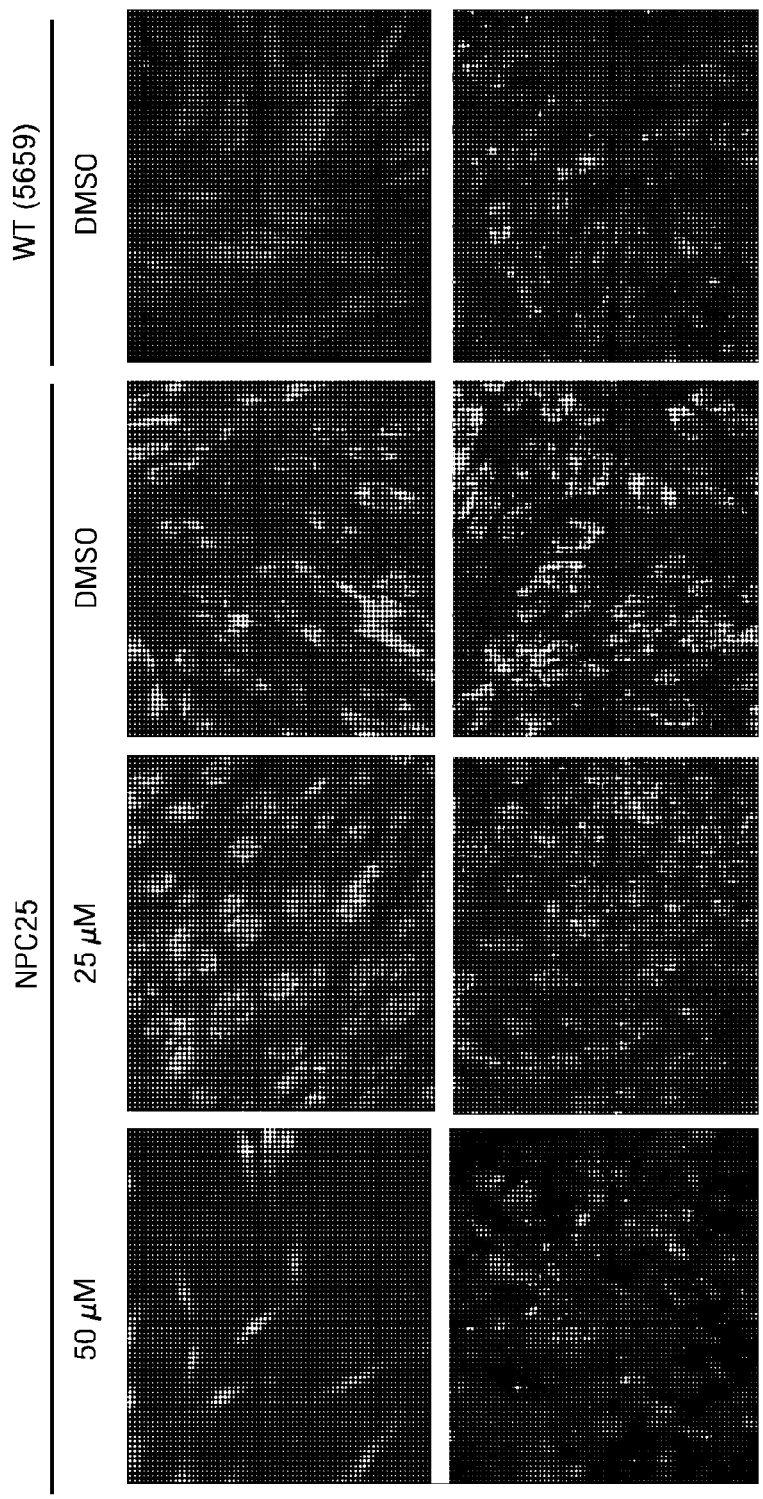

Free cholesterol accumulation in cells is a hallmark of NPC disease. The Amplex red cholesterol assay was used to screen an approved drug library in the NPC patient-derived skin fibroblasts that have free cholesterol accumulation in late endosome and lysosome. Surprisingly, we disclose δ-tocopherol. δ-tocopherol significantly reduced the cholesterol amount in the NPCD fibroblasts. This cholesterol reduction effect was concentration dependent and proportional to the time of compound treatment (2 to 5 days) to the cells (FIG. 1a). We then show δ-tocopherol in the filipin cholesterol staining assay, a method used clinically for NPCD diagnosis. We disclose the cholesterol reduction effect of δ-tocopherol and free cholesterol accumulation in NPCD patient cells was significantly reduced (FIG. 1b). Lysosome size is usually enlarged in the NPCD cells using a lysotracker staining assay. As shown in FIG. 1c, the enlarged lysosome size in NPCD fibroblasts was decreased and shrunken to the size similar to the wild type cells. These effects on free cholesterol amount, filipin cholesterol staining, and lysotracker staining observed for δ-tocopherol were more significant and potent than any of the other vitamin E isoforms. The effects of cholesterol reduction and lysosome size decrease by δ-tocopherol in the NPC fibroblasts required a compound treatment for 2 to 5 days with a significant effect after the 4-5 day treatment. δ-tocopherol at 40 μM was more potent than α-tocopherol at 80 μM.

We disclose δ-tocopherol in 9 additional fibroblast primary cells derived from different NPCD patients using above assays to examine the potential variability in the cells derived from different NPCD patients. No significant difference was found in these cells and the effects on cholesterol reduction and lysosome size decrease were confirmed in all of these patient cells. Similar to the initial experimental results, the effect of δ-tocopherol was more potent than that of α-tocopherol in all these cells.

Figure 2A:
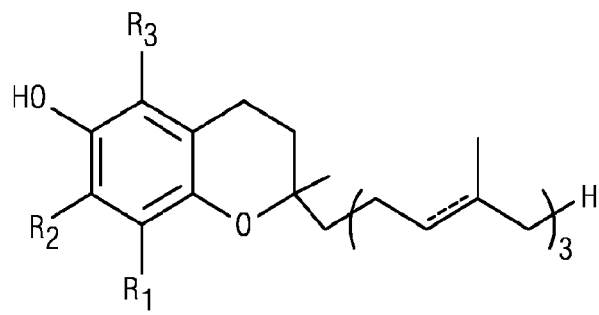
FIG. 2. A) Structures of vitamin E analogs. B) The influence of different forms of vitamin E on free cholesterol level of NPC cells. C) The influence of other vitamins and antioxidants on the free cholesterol level of NPC cells. D) The influence of various compounds in cellular ATP level of NPC cells. E) Delta-tocopherol treatment did not change the expression level of NPC1 and HMG-CoA reductase in NPC fibroblasts.
Figure 2B:
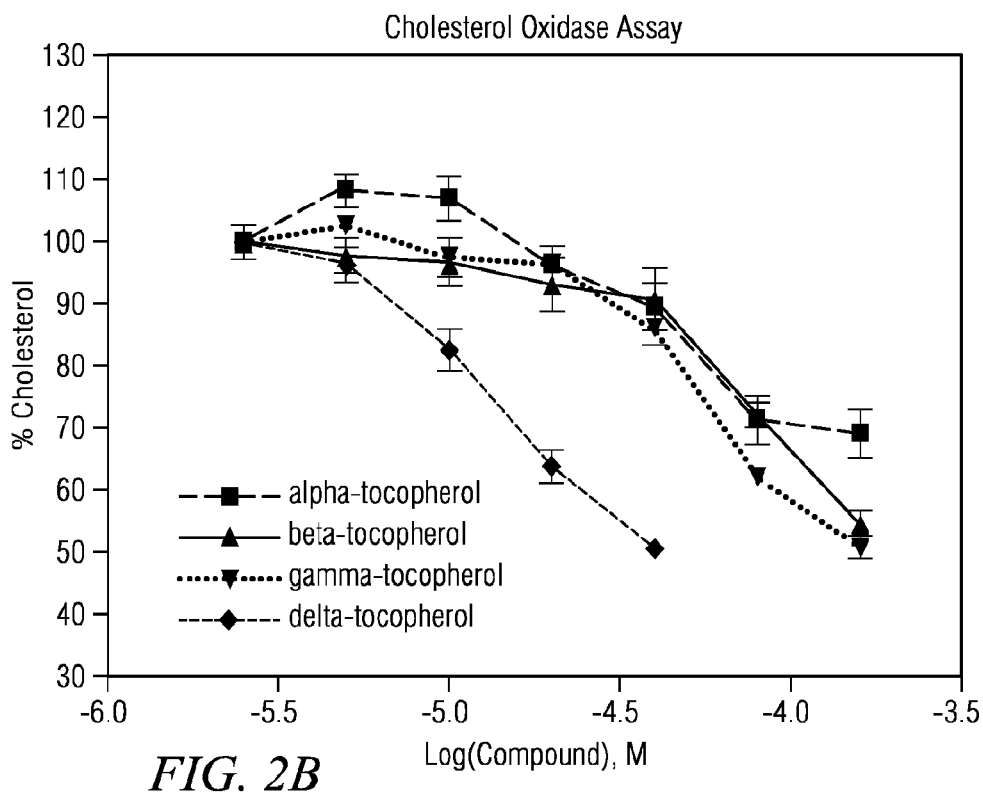
Figure 2C:
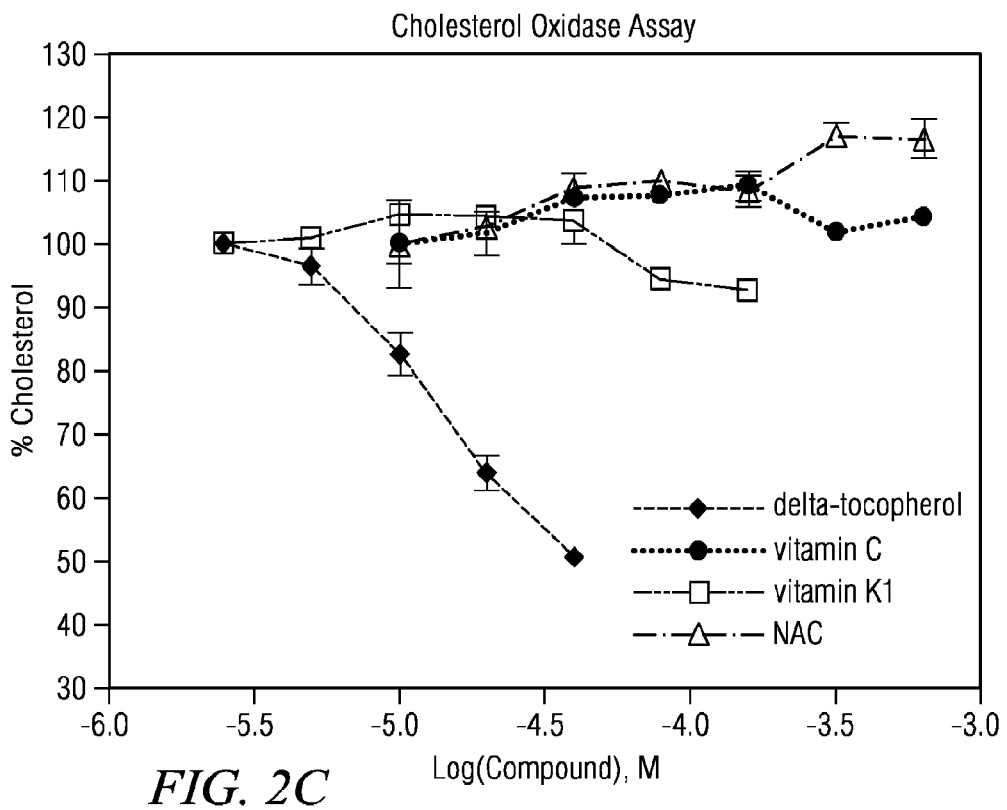

In order to examine if the cholesterol reduction effect of tocopherols was related to an antioxidant effect, we tested a potent antioxidant agent N-acetyl cysteine (NAc) in the same set of assays. We found that NAc did not have any effect on the cholesterol reduction nor lysosome size decrease (FIG. 2c), indicating that antioxidant effect of vitamin E may not account for the effects we observed on these NPCD cells. We also found that the other lipid soluble and water soluble vitamins including vitamin D, vitamin K, and vitamin C were not active in these assays further teaching that the effects of δ-tocopherol on cholesterol reduction and lysosome size decrease were specific and were not generalized in other vitamins (FIG. 2c). We disclose that the compound's cytotoxicity could interfere with these cell-based assays that often appeared as the false positives for cholesterol reduction and lysosome size decrease. We show that the cytotoxicity of compounds with the cell/nuclear dye co-staining methods and an ATP content assay in parallel with the cholesterol and lysotracker assays. Cytotoxicity was not present at the effective concentration of these δ-tocopherol (FIG. 2d). δ-tocopherol, at a concentration of 50 uM or less did not show significant cytotoxicity after up to a 5-day compound treatment. We found that the impure compound preparation in combination with too high of a concentration of tocopherols could lead to the significant cytotoxicity in both wild type and NPCD fibroblasts. Although the tocotrienol effect on these NPCD cells were observed, they were more toxic in our assays and the additional compound purification (to 99%).

Figure 2D:
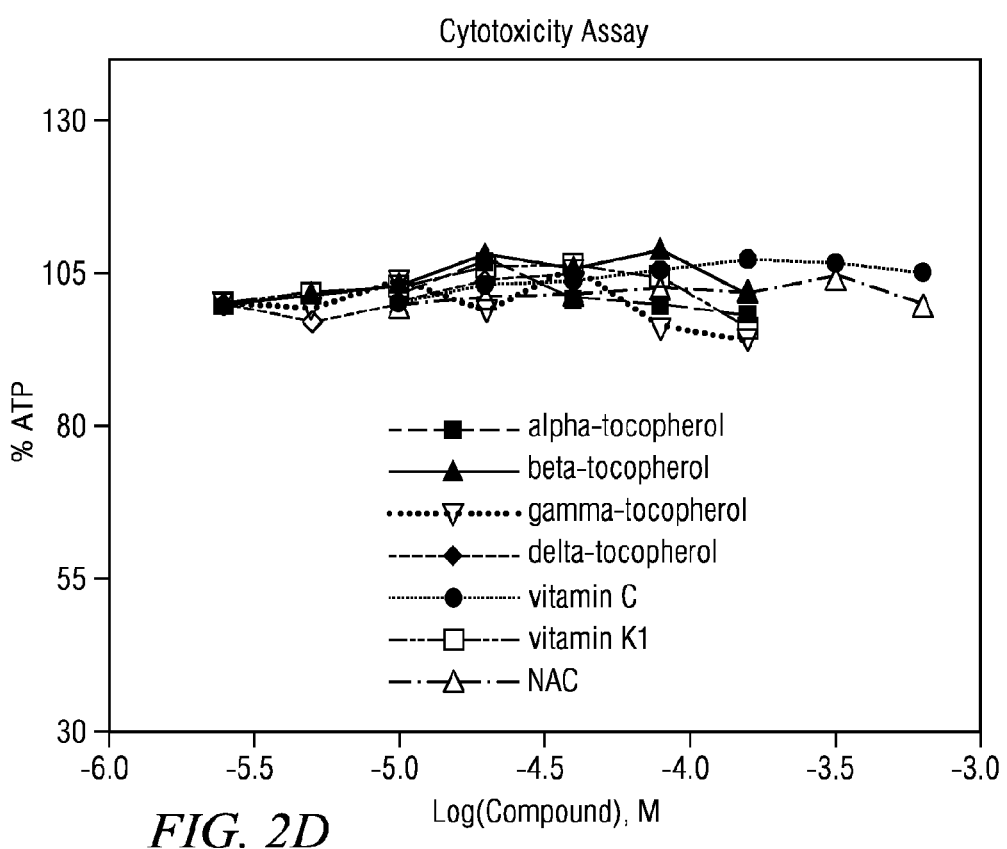
Figure 2E:
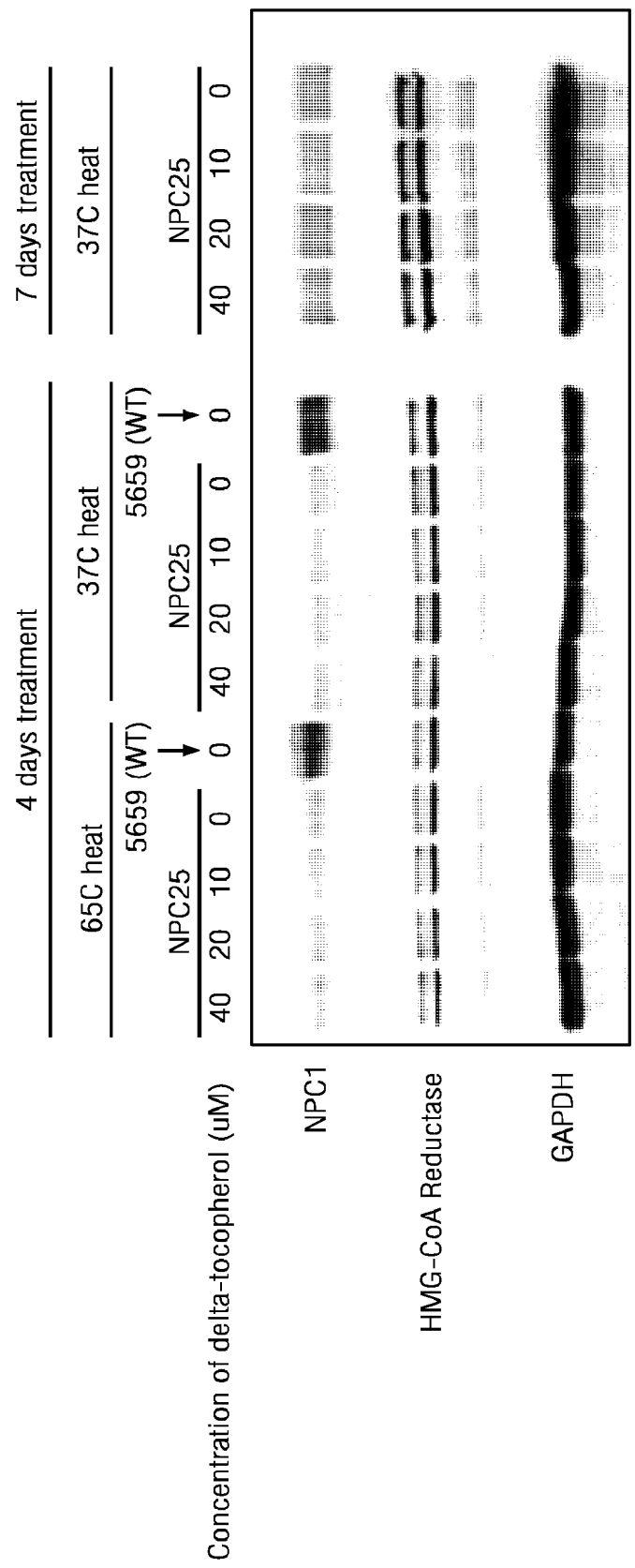

It has been reported that the inhibition of cholesterol de novo synthesis and increase in NPC protein expression might correct the phenotype in these NPCD cells. In addition, the over expression of Rab9 or acid sphingomyelinase has been reported to reduce the cholesterol accumulation in the NPCD cells. We found that neither the expression of HMG-CoA reductase, a key enzyme in the cholesterol synthesis pathway, nor that of NPC-1 protein was changed by the δ-tocopherol treatment (FIG. 2d). The activity of HMG-CoA reductase or acid sphingomyelinase was not changed as well. The Rab9 and acid sphingomyelinase protein levels remained same in these cells after the treatment with the δ-tocopherol (FIG. 2d). We therefore disclose that these proteins may not be directly involved in the mechanism of action of the δ-tocopherol treatment as it relates to cholesterol reduction and lysosome size decrease. Thus, we further disclose a pathway for lipid recycling/membrane movement in the membrane system which is enhanced by the δ-tocopherol treatment. Through this enhanced lipid recycling pathway, the clearance of the accumulated free cholesterols in lysosome occurs resulting in the decrease in lysosome size in these NPCD cells.

Skin fibroblasts derived from patients with lysosomal storage diseases are commonly used for clinic diagnosis. They are also readily available from Coriell Cell Repository and can be passaged up to 20-30 times in cell culture. Although not all the patient derived fibroblasts exhibit lysosomal storage of macromolecules, the lipid storage and enlargement of lysosome size are showed in fibroblasts from patients with Farber, Niemann-Pick type A, Wolman, and Tay Sachs disease. We found that the enlargement of lysosome size in these four types of fibroblasts can be measured by the lysotracker dye staining method, similarly to that used in the cells obtained from patients with Niemann-Pick type C disease. These patient derived fibroblasts can be used as the disease models for drug testing. Farber, Niemann-Pick Type A, Wolman and Tay Sachs diseases caused accumulation of ceramide, sphingomyelin, cholesterol-ester and GM2 gangliosides accumulation in lysosomes, respectively. (See FIGS. 8-23).

Figure 3:
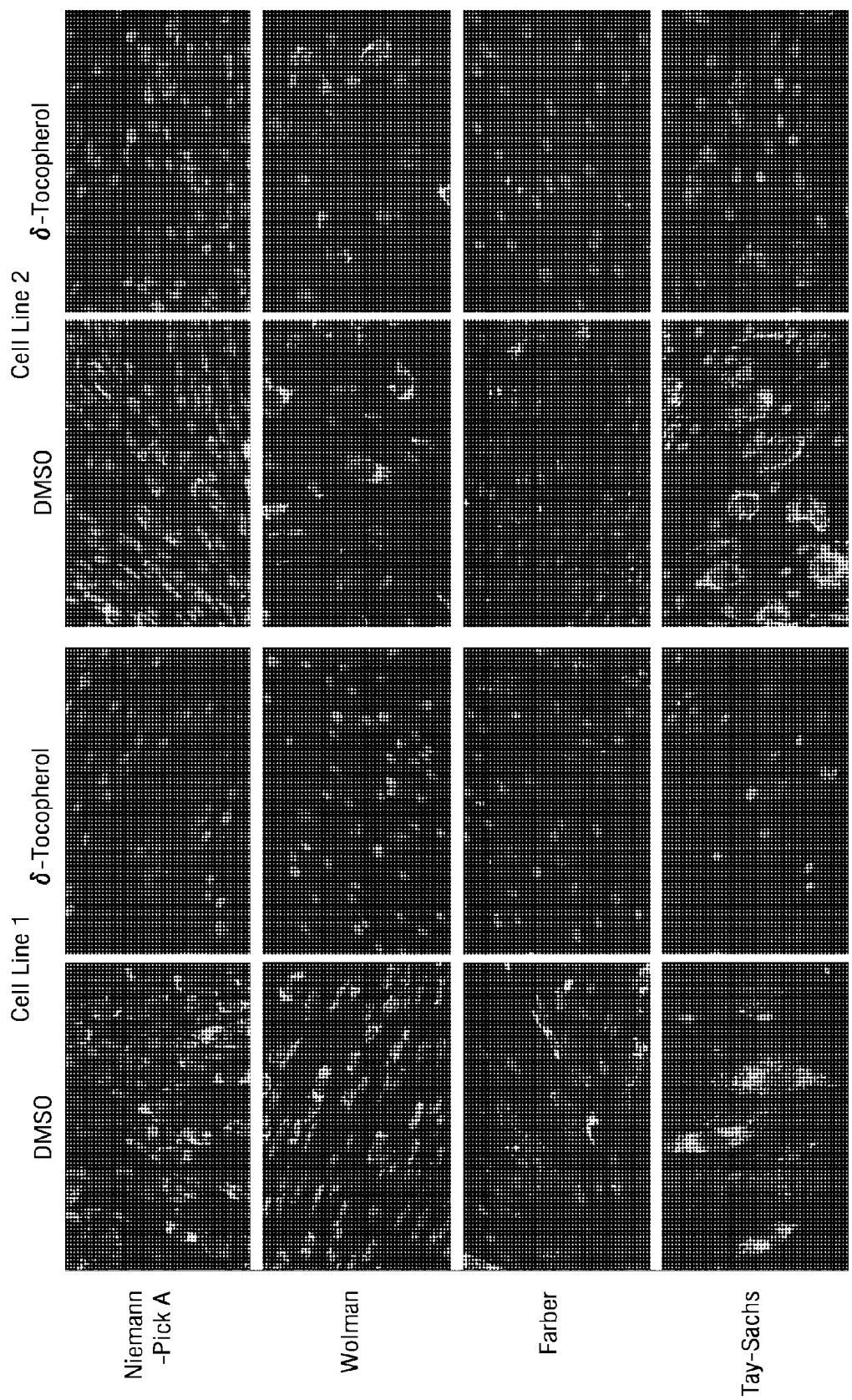
FIG. 3. Lysotracker staining of lysosomal storage disease cells treated with δ-tocopherol. Cells were treated similarly as in FIG. 1 and stained by Lysotracker Red and Hoechst as described in the method session.

Four other types of patient derived skin fibroblasts were tested in the lysotracker assay that visualizing the acidic compartments inside cells including late endosome and lysosome. We disclose that δ-tocopherol significantly reduced the size of enlarged lysosomes in all four cell types including these of Niemann Pick type A, Wolman, Farber and Tay-Sachs diseases (FIG. 3, see also FIGS. 8-23). These cell types a distinct lysosomal storage disorders with the enlarged lysosomes in cells. Cholesterol esters instead of free cholesterols are accumulated in lysosomes of Wolman disease due to the mutations of acid lipase. Niemann Pick type A disease is caused by deficiency in acid sphigomyelinase (ASM) activity which results in accumulation of sphingomyelin in lysosomes. Ceramides, produced by ASM from sphingomyelin, accumulated in lysosomes as a result of ceramidase deficiency in Farber disease. Tay-Sachs is caused by the hexosaminidase A deficiency and accumulation of GM2 lipids in lysosomes. The structures of these lipids involving these four additional lysosomal storage diseases are different from free cholesterol. We disclose the use of δ-tocopherol on the lysosome size decrease in all of these diseases. We further disclose in an alternate embodiment, that δ-tocopherol inserts into the membrane and facilitates the movement of accumulated lipids out of lysosome resulting in a decrease in the enlarged lysosome size in these cells.

Figure 4A:
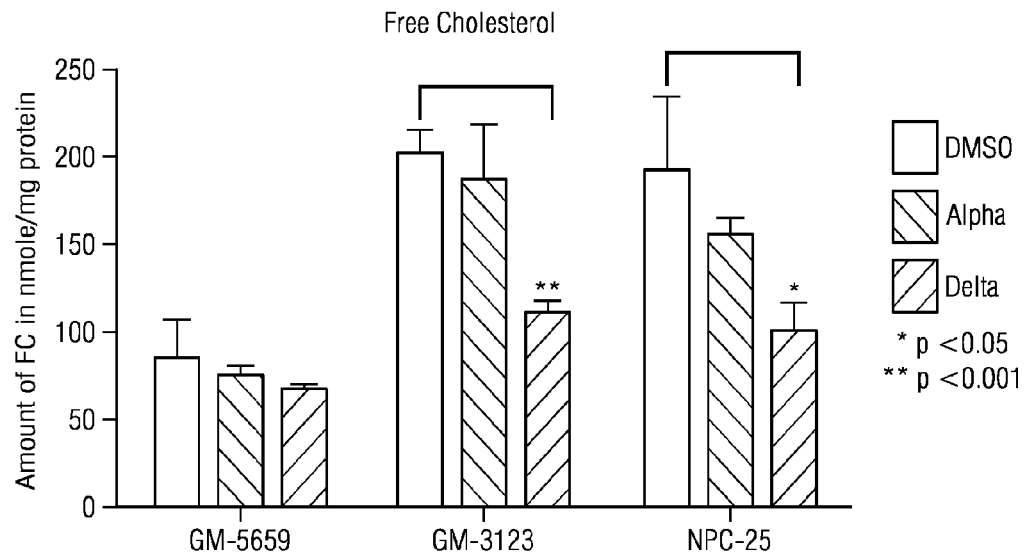
FIG. 4. Effects of δ-tocopherol and α-tocopherols on (A) free cholesterol, (B) cholesterol ester and (C) sphingomyeline in NPC cells. NPC or WT cells were treated with DMSO, 80 uM α-tocopherol or 40 uM δ-tocopherol for 5 days. Cell pellets were collected and extracted for lipids. FC EC and sphingomyeline levels were measured by GC/MS. (D) Effects of of δ-tocopherols and α-tocopherols on cholesterol efflux.
Figure 4B:
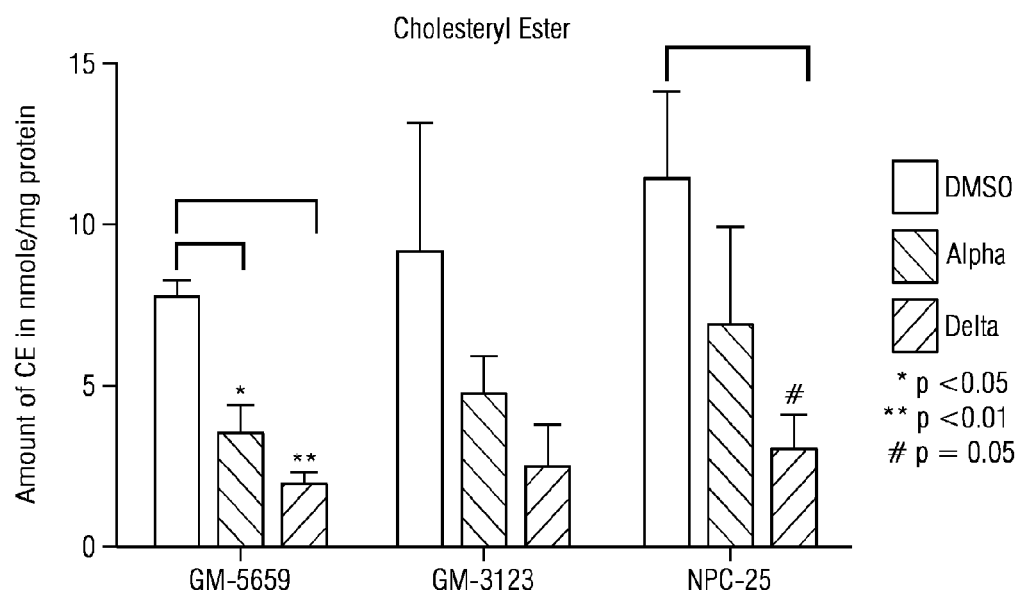
Figure 4C:
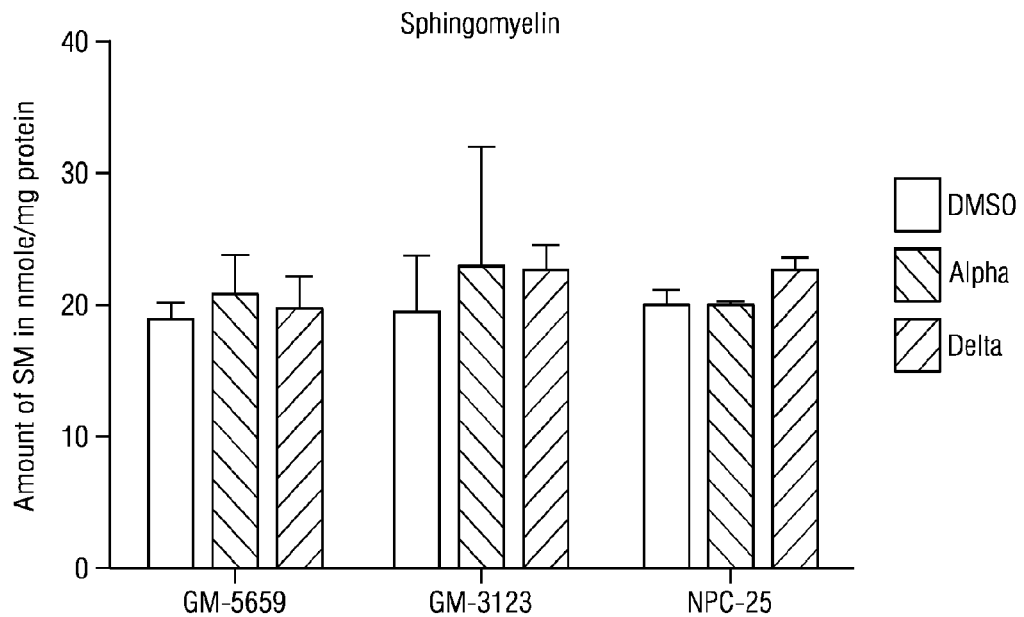
Figure 4D:
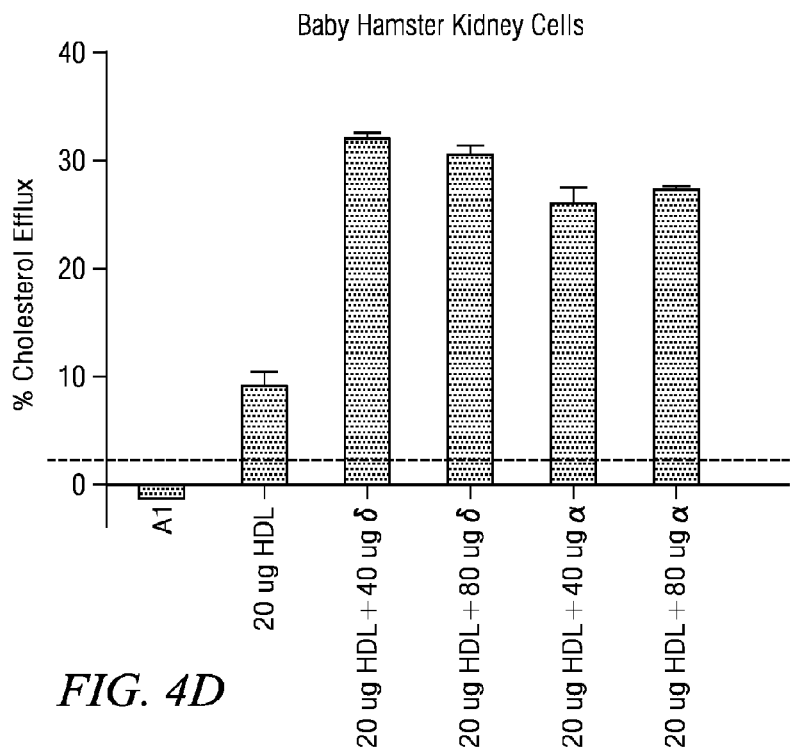

The direct measurements using a GC-MS method revealed that the free cholesterol was reduced in the NPC fibroblasts after δ-tocopherol treatment in NPCD fibroblasts (FIG. 4a). The effect of δ-tocopherol was profound in the free cholesterol level in NPCD cells was nearly recovered to the normal level as in the wild type cells (FIG. 4a), while the effect of α-tocopherol was not statistically different due to the high variation among the three test groups. The free cholesterol level in normal cells was also reduced slightly after the treatment. The amount of cholesterol ester in both NPCD and wild cells after the treatments of both α- and δ-tocopherol was significantly reduced (FIG. 4b). The sphingomyelin amount in both cell types was not significantly changed after the treatment (FIG. 4c). We also show that the cholesterol efflux significantly increased after the treatments with δ-tocopherol in the baby hamster kidney cells (FIG. 4d), indicating the free cholesterols removed from late endosomes and lysosomes were transferred out of cells via the increased cholesterol efflux. Thus, we disclose δ-tocopherol facilitates the lipid movement in membrane. The reduction of intracellular free cholesterol as the result of increased cholesterol efflux by δ-tocopherol mobilizes the storage cholesterol or the utilization of storage cholesterols is also enhanced by δ-tocopherol.

Figure 5A:
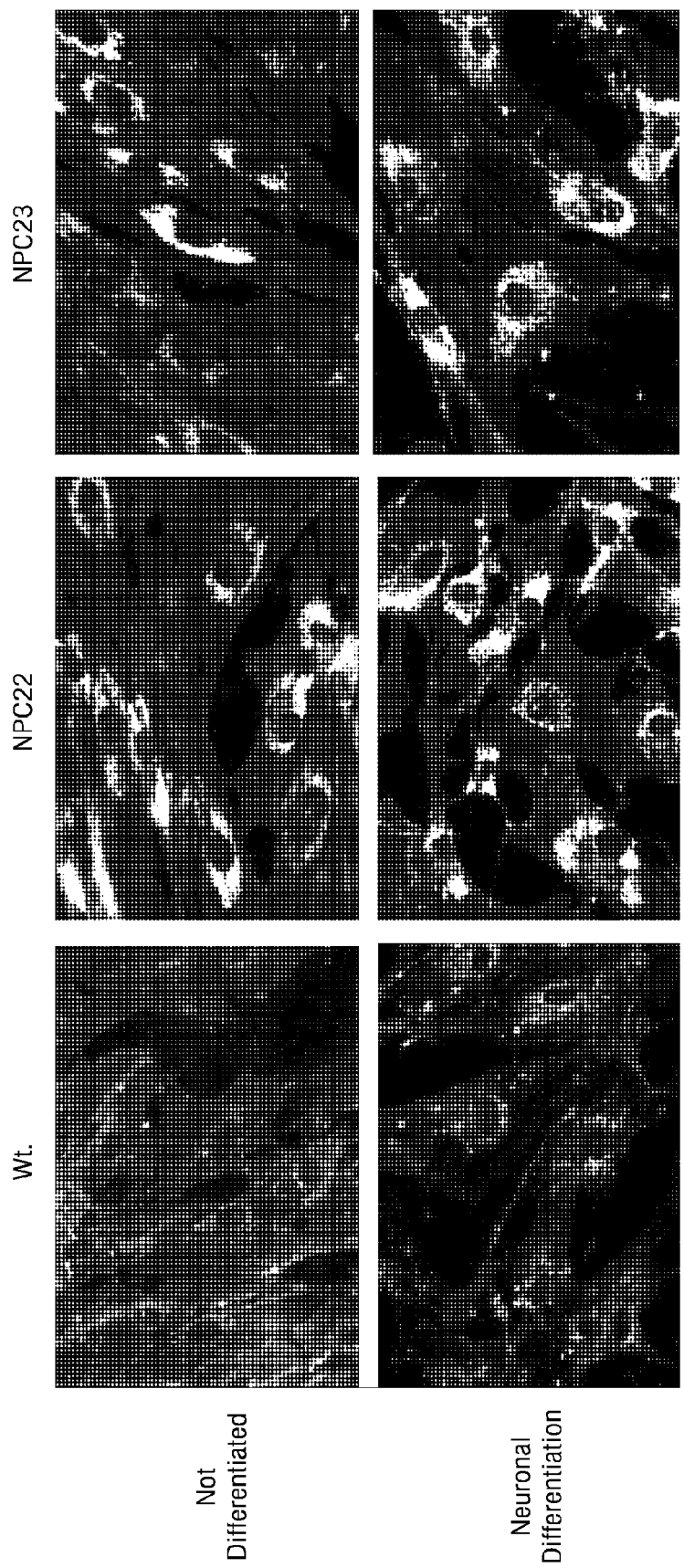
FIG. 5. A) Filipin staining of the WT or NPC MSC cells. B) NPC cells treated with δ-tocopherol or DMSO were co-stained with filipin and the antibody against neuronal beta III tubulin. Cells were treated and stained as described in the method section.
Figure 5B:
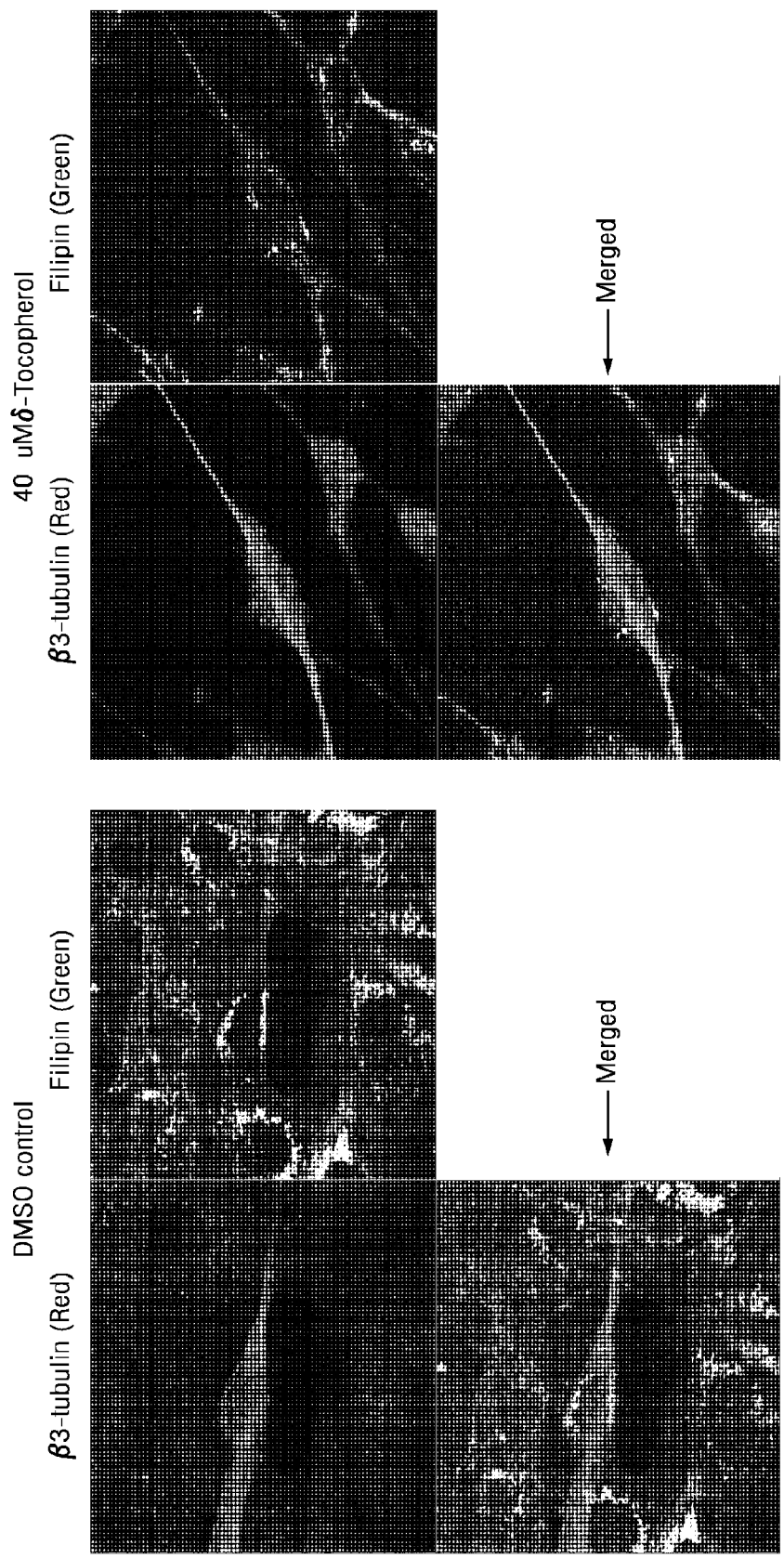
Figure 6:
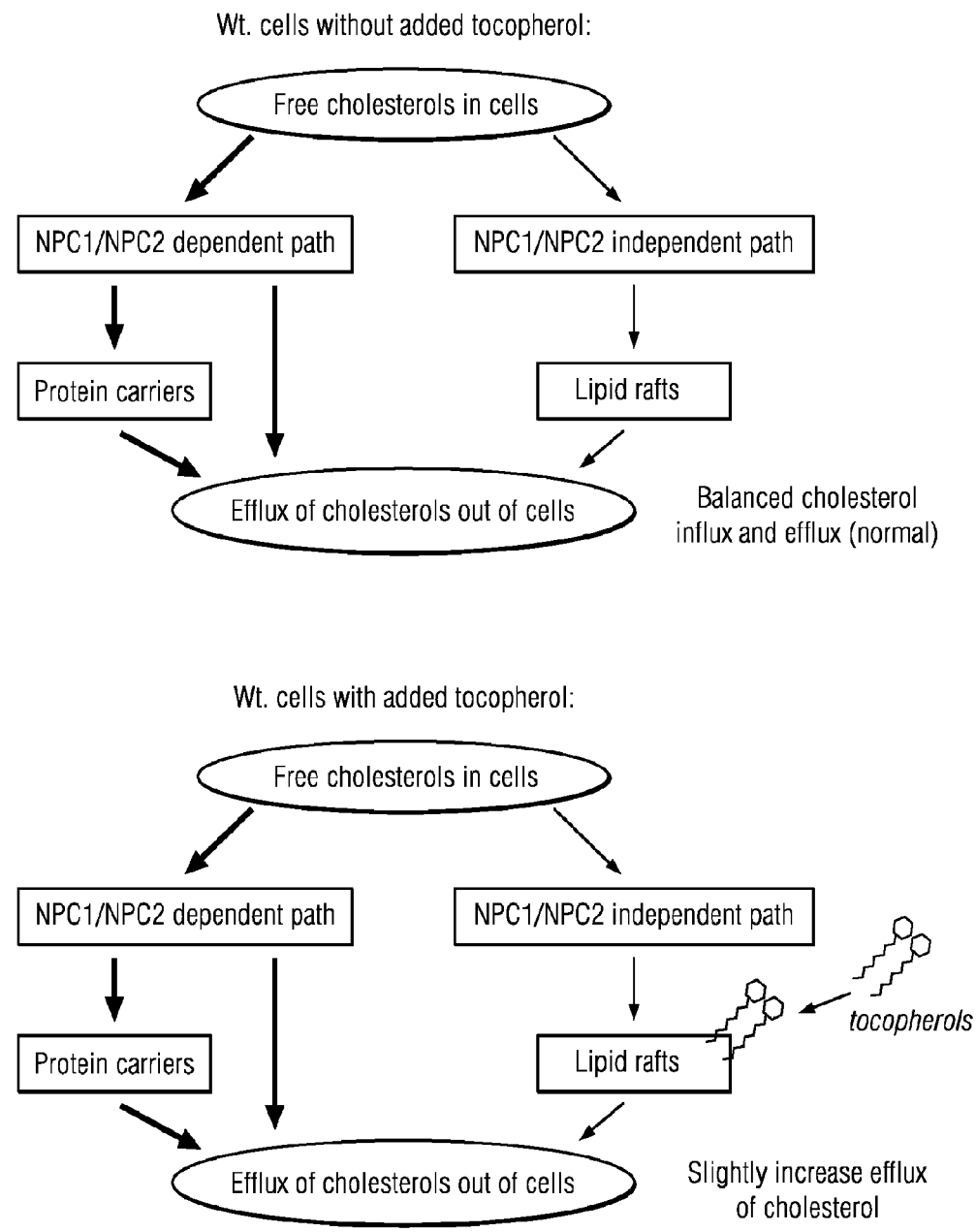
FIG. 6. A model for mechanism of action for tocopherols.
Figure 7:
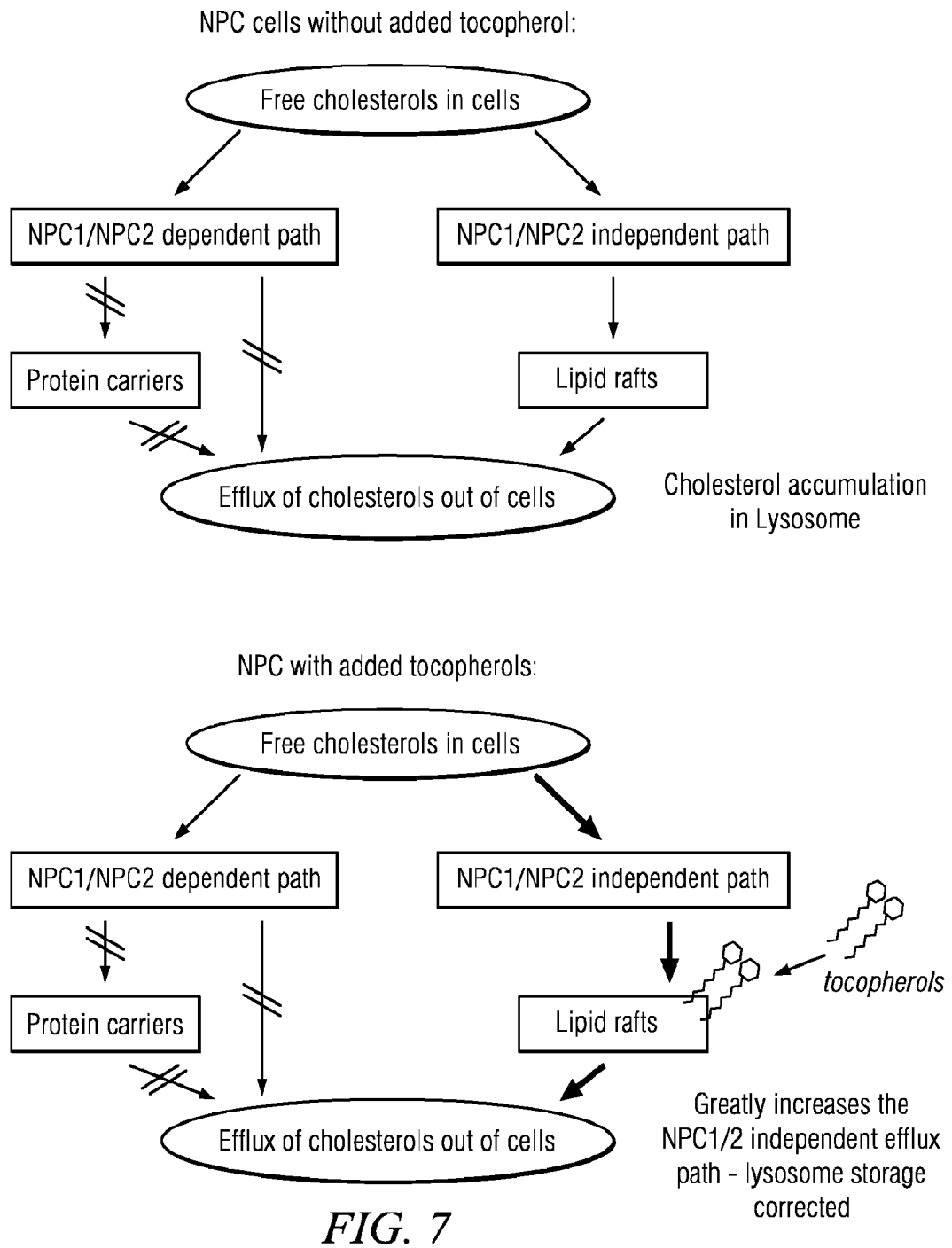
FIG. 7. A model for mechanism of action for tocopherols.
Figure 8:
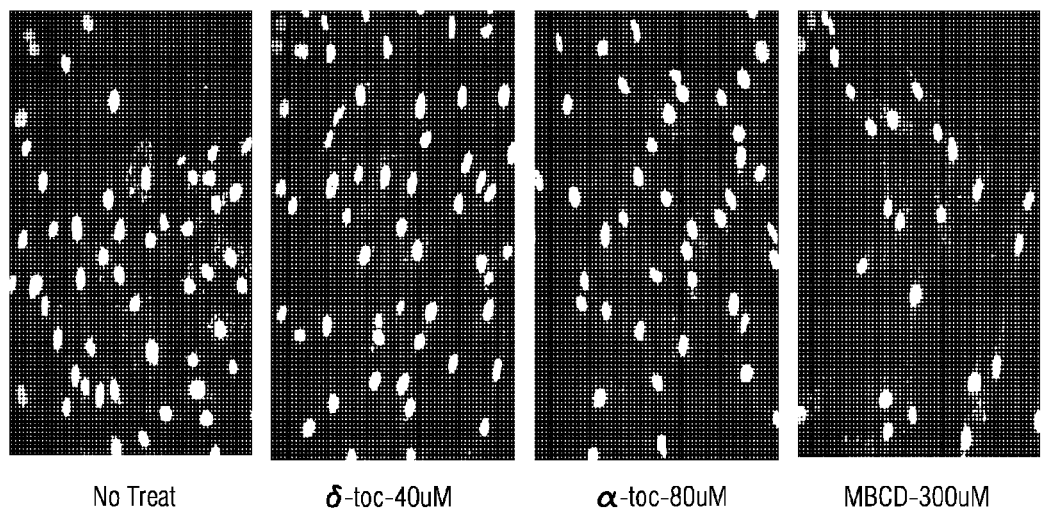
FIG. 8. Lysotracker staining images from WT (wild type) control cells are in the top panel and from Farber disease fibroblasts are in the bottom panel. Drugs (80 uM alpha-tocopherol, 40 uM delta-tocopherol and 300 uM methyl-beta-cyclodextrin) were treated for four days in cell culture. 40× objectives.
Figure 8:
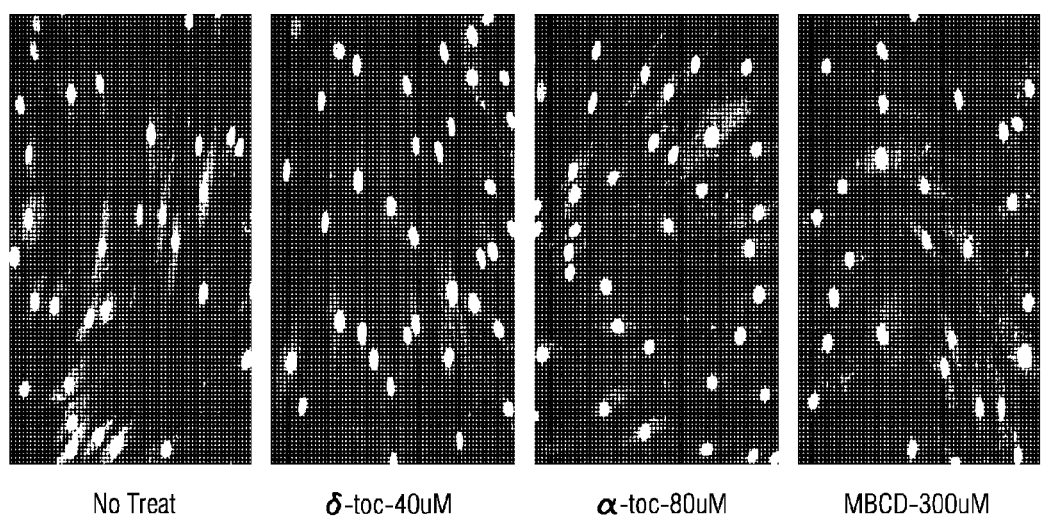
Figure 9:
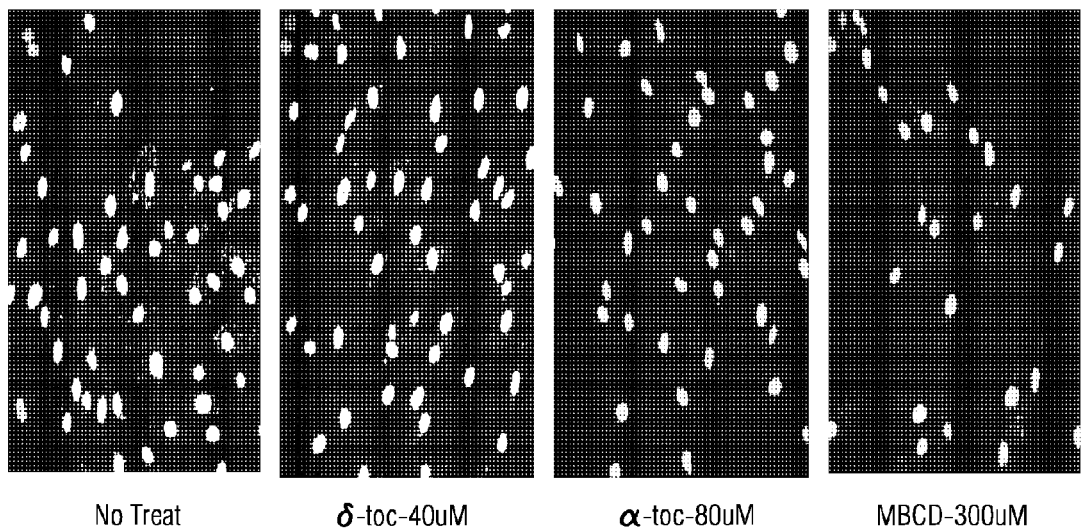
FIG. 9. Lysotracker staining images from WT (wild type) control cells are in the top panel and from Niemann Pick Type A disease (NPA) fibroblasts are in the bottom panel. Drugs (80 uM alpha-tocopherol, 40 uM delta-tocopherol and 300 uM methyl-beta-cyclodextrin) were treated for four days in cell culture. 40× objectives.
Figure 9:
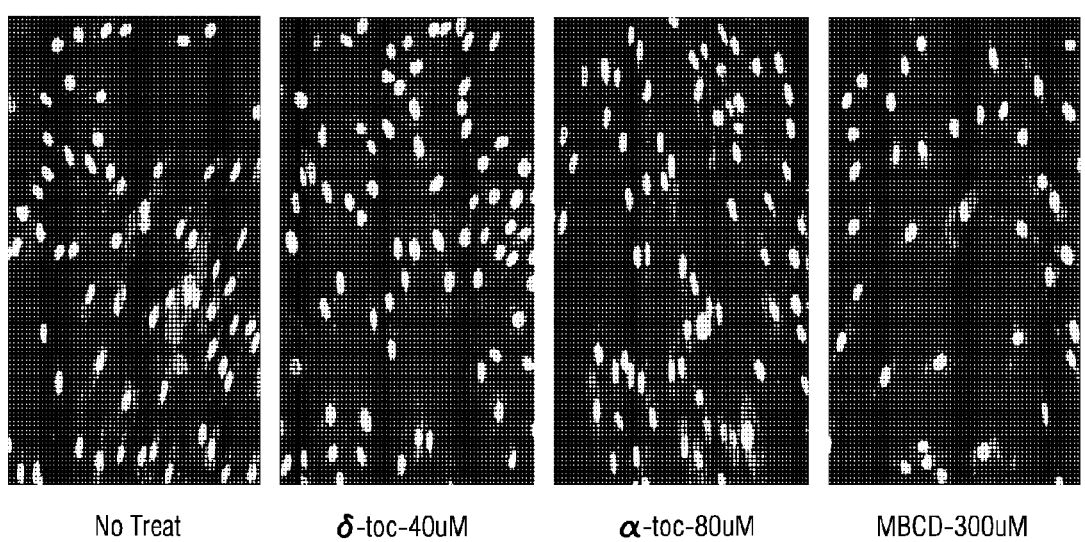
Figure 10:
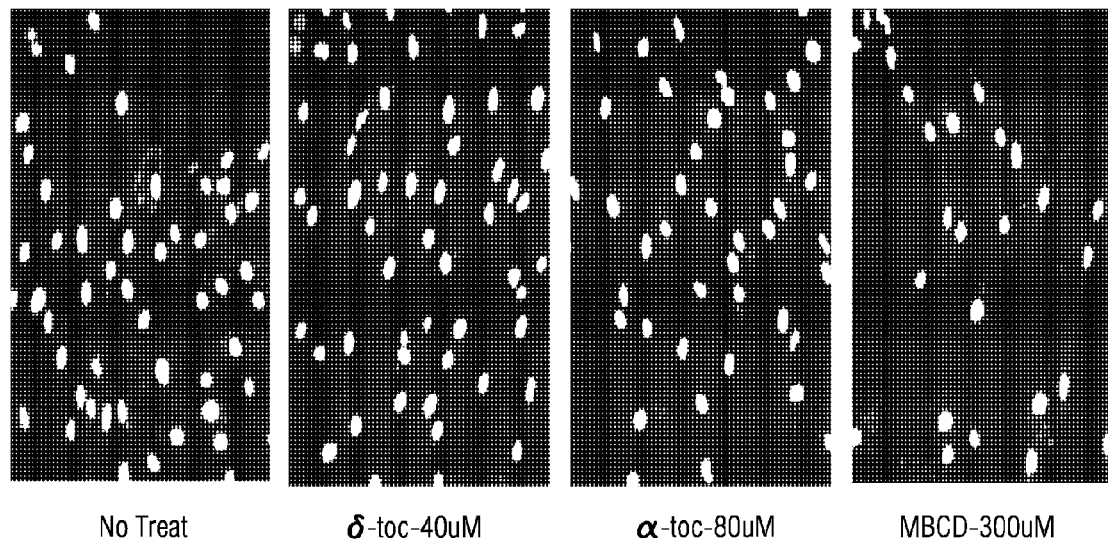
FIG. 10. Lysotracker staining images from WT (wild type) control cells are in the top panel and from Wolman6144 disease fibroblasts (from two patients) are in the bottom panel. Drugs (80 uM alpha-tocopherol, 40 uM delta-tocopherol and 300 uM methyl-beta-cyclodextrin) were treated for four days in cell culture. 40× objectives.
Figure 10:
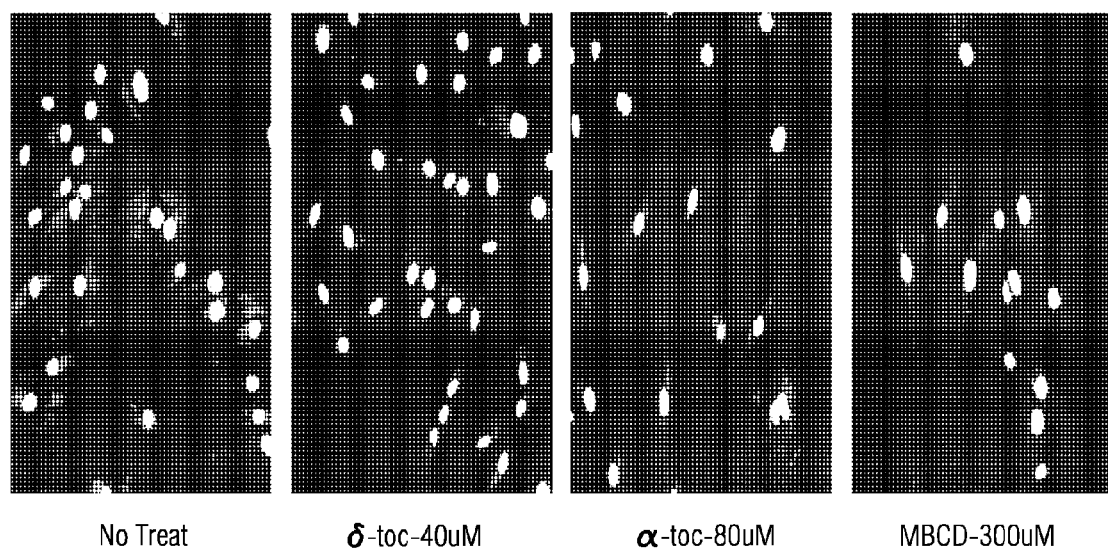
Figure 11:
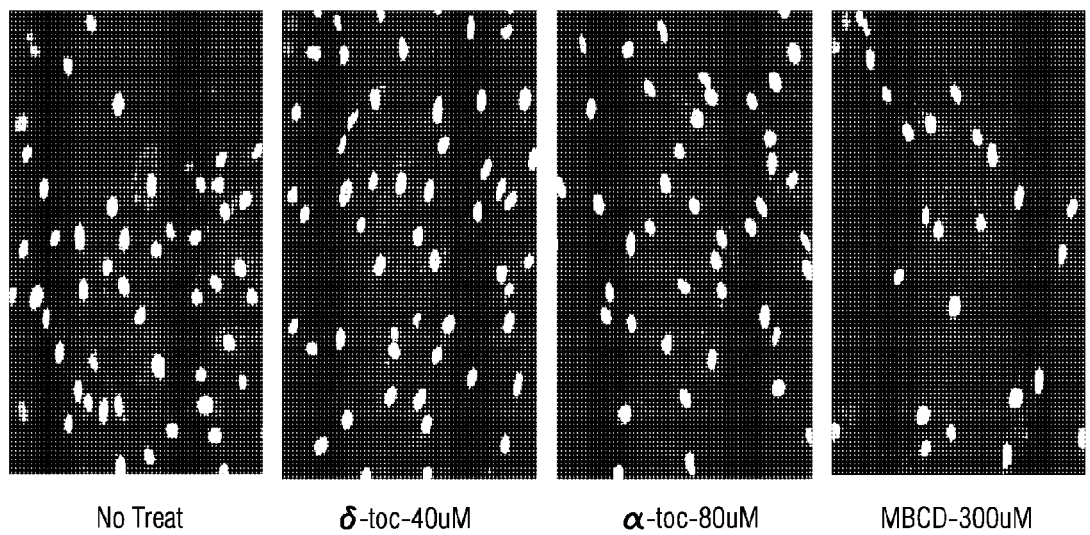
FIG. 11. Lysotracker staining images from WT (wild type) control cells are in the top panel and from Wolman11851 disease fibroblasts (from two patients) are in the bottom panel. Drugs (80 uM alpha-tocopherol, 40 uM delta-tocopherol and 300 uM methyl-beta-cyclodextrin) were treated for four days in cell culture. 40× objectives.
Figure 11:
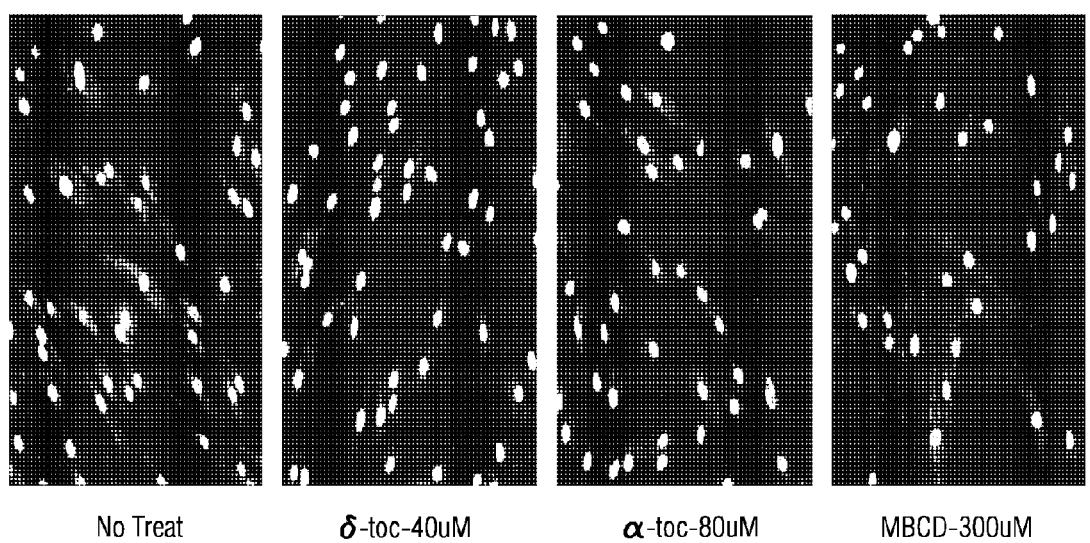
Figure 12:
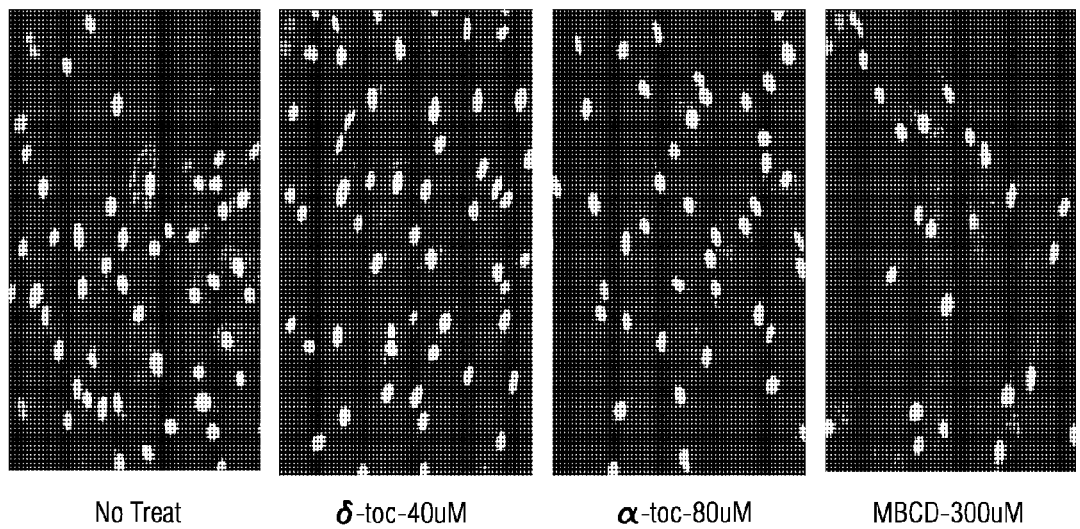
FIG. 12. Lysotracker staining images from WT (wild type) control cells are in the top panel and from Tay Sachs disease fibroblasts are in the bottom panel. Drugs (80 uM alpha-tocopherol, 40 uM delta-tocopherol and 300 uM methyl-beta-cyclodextrin) were treated for four days in cell culture. 40× objectives.
Figure 12:
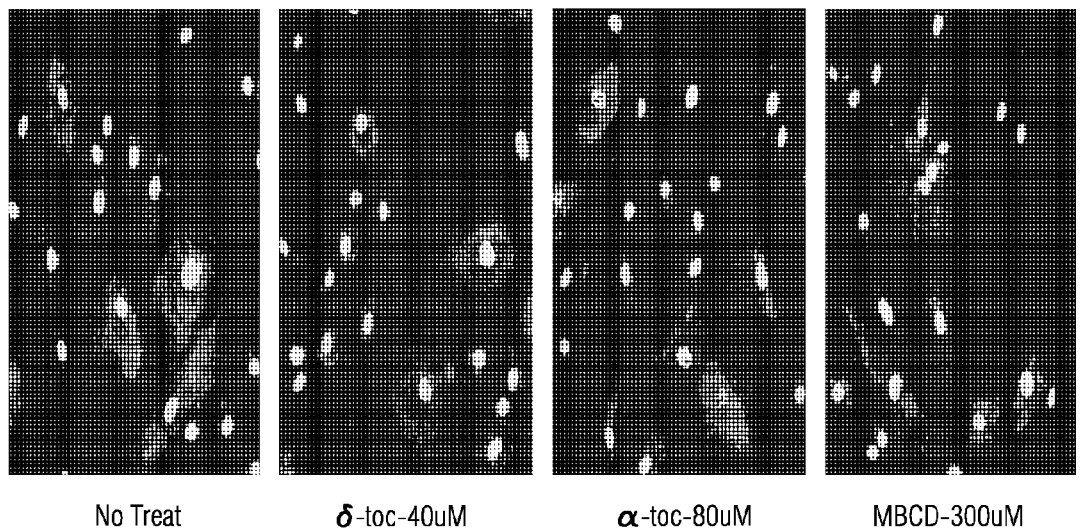
Figure 13:
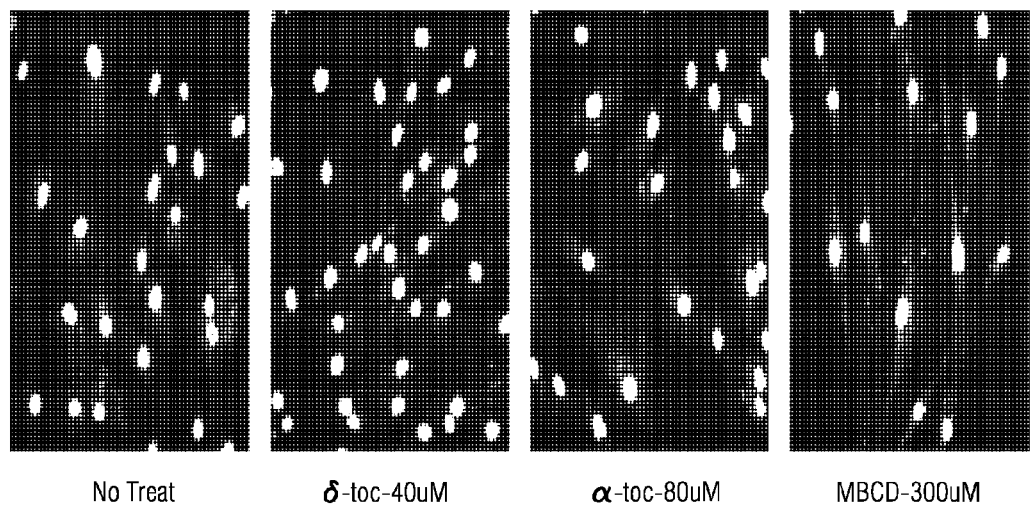
FIG. 13. Lysotracker staining images from WT (wild type) control cells are in the top panel and from Farber disease fibroblasts are in the bottom panel. Drugs (80 uM alpha-tocopherol, 40 uM delta-tocopherol and 300 uM methyl-beta-cyclodextrin) were treated for four days in cell culture. 20× objectives.
Figure 13:
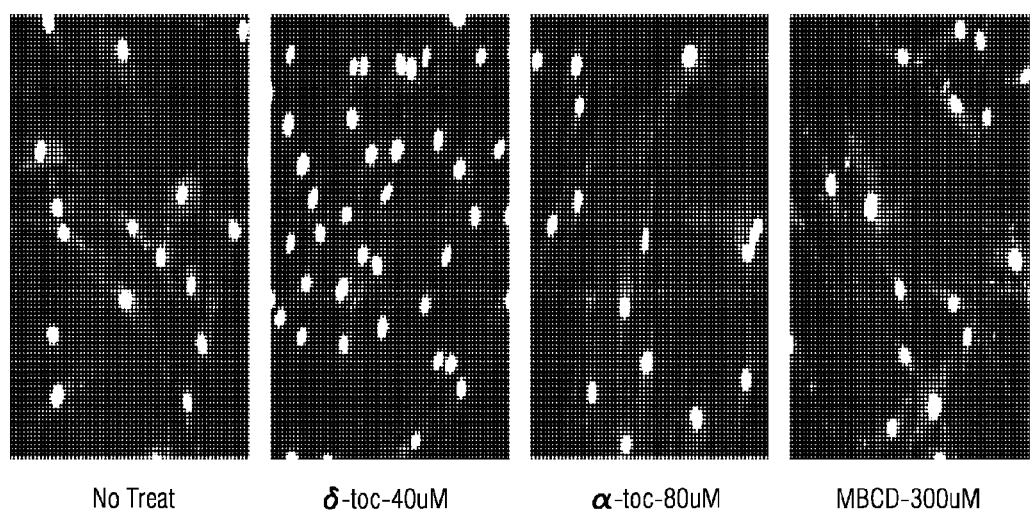
Figure 14:
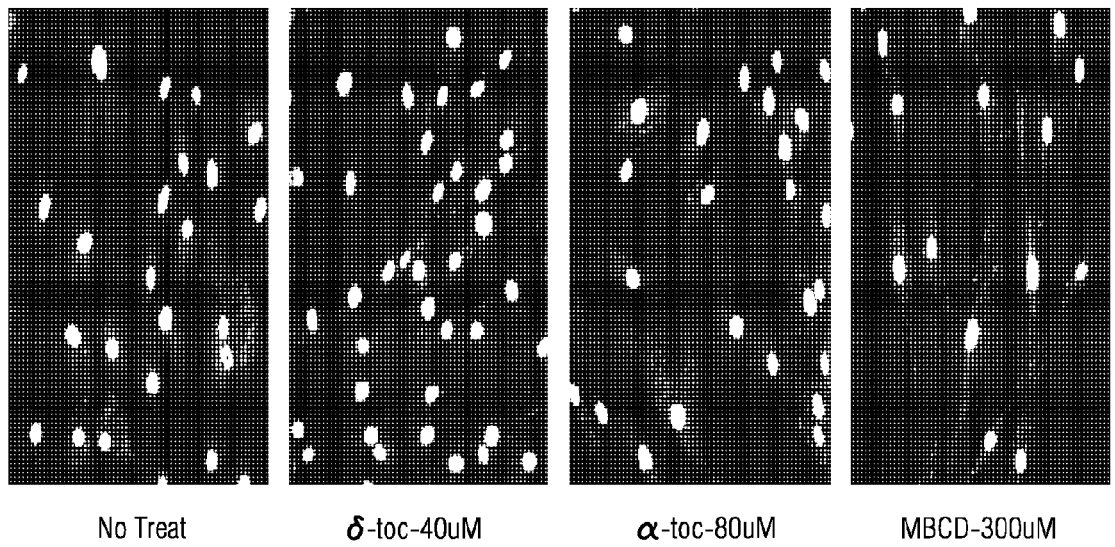
FIG. 14. Lysotracker staining images from WT (wild type) control cells are in the top panel and from Niemann Pick Type A disease (NPA) fibroblasts are in the bottom panel. Drugs (80 uM alpha-tocopherol, 40 uM delta-tocopherol and 300 uM methyl-beta-cyclodextrin) were treated for four days in cell culture. 20× objectives.
Figure 14:
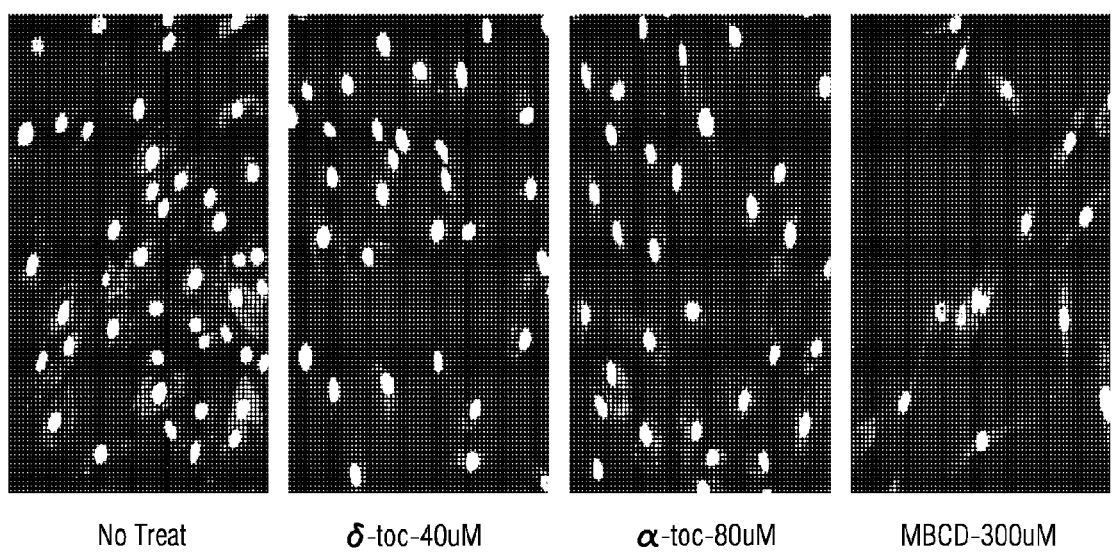
Figure 15:
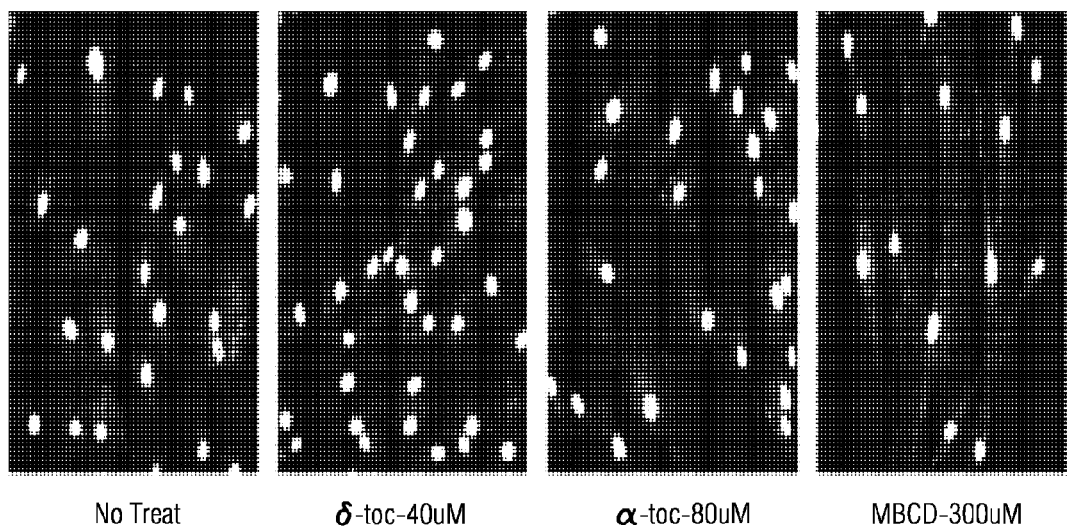
FIG. 15. Lysotracker staining images from WT (wild type) control cells are in the top panel and from Wolman6144 disease fibroblasts (from one patient) are in the bottom panel. Drugs (80 uM alpha-tocopherol, 40 uM delta-tocopherol and 300 uM methyl-beta-cyclodextrin) were treated for four days in cell culture. 20× objectives.
Figure 15:
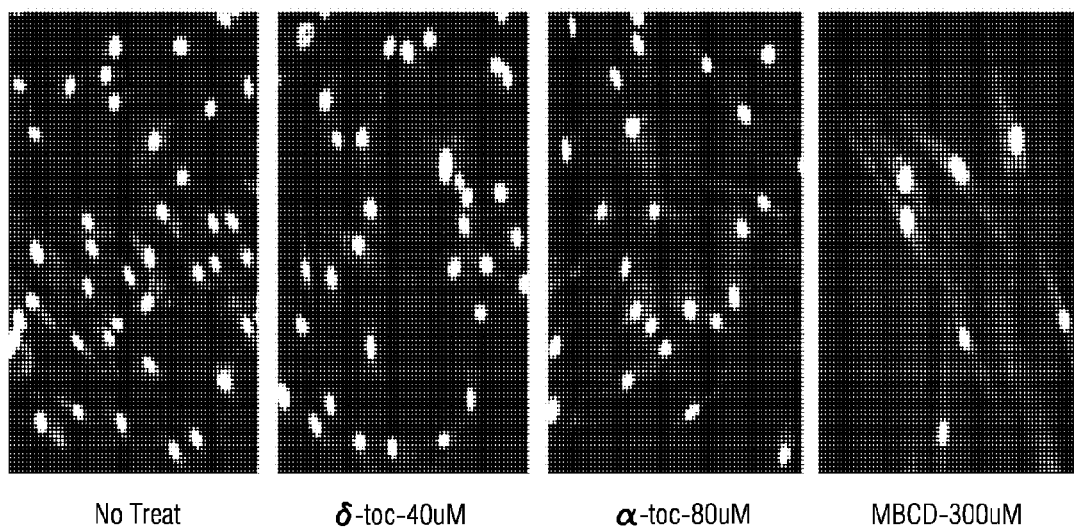
Figure 16:
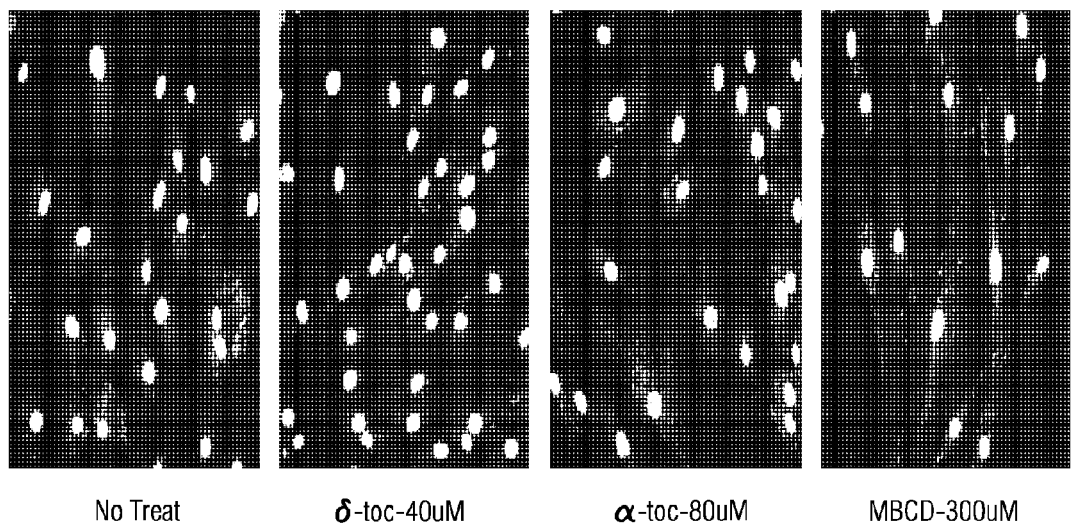
FIG. 16. Lysotracker staining images from WT (wild type) control cells are in the top panel and from Wolman11851 disease fibroblasts (from one patient) are in the bottom panel. Drugs (80 uM alpha-tocopherol, 40 uM delta-tocopherol and 300 uM methyl-beta-cyclodextrin) were treated for four days in cell culture. 20× objectives.
Figure 16:
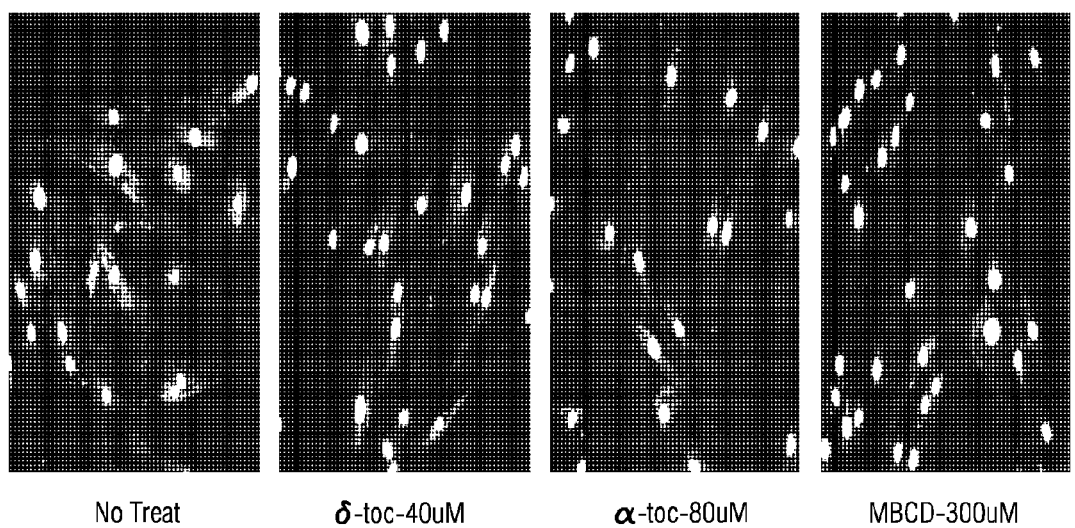
Figure 17:
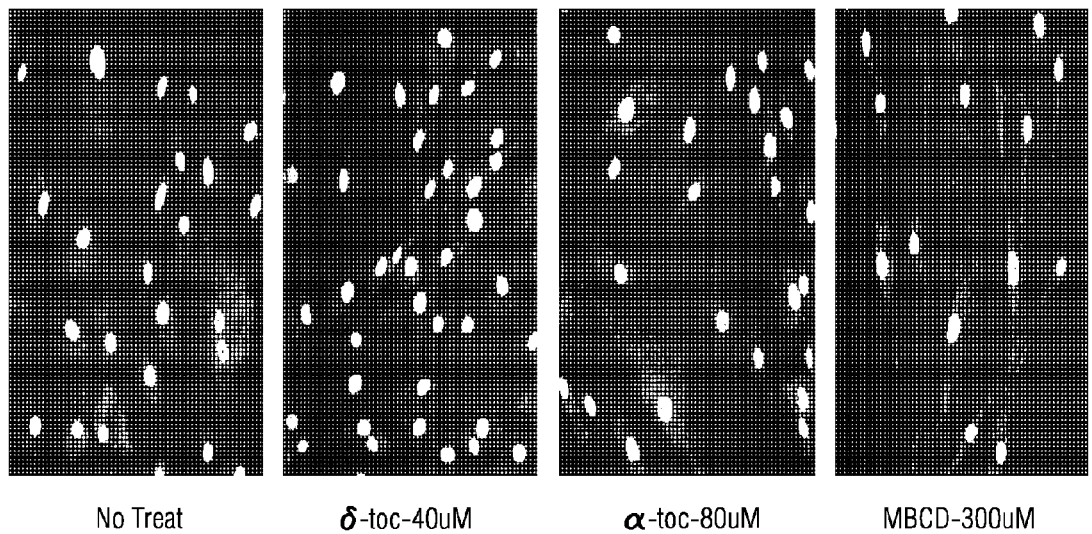
FIG. 17. Lysotracker staining images from WT (wild type) control cells are in the top panel and from Tay Sachs disease fibroblasts are in the bottom panel. Drugs (80 uM alpha-tocopherol, 40 uM delta-tocopherol and 300 uM methyl-beta-cyclodextrin) were treated for four days in cell culture. 20× objectives.
Figure 17:
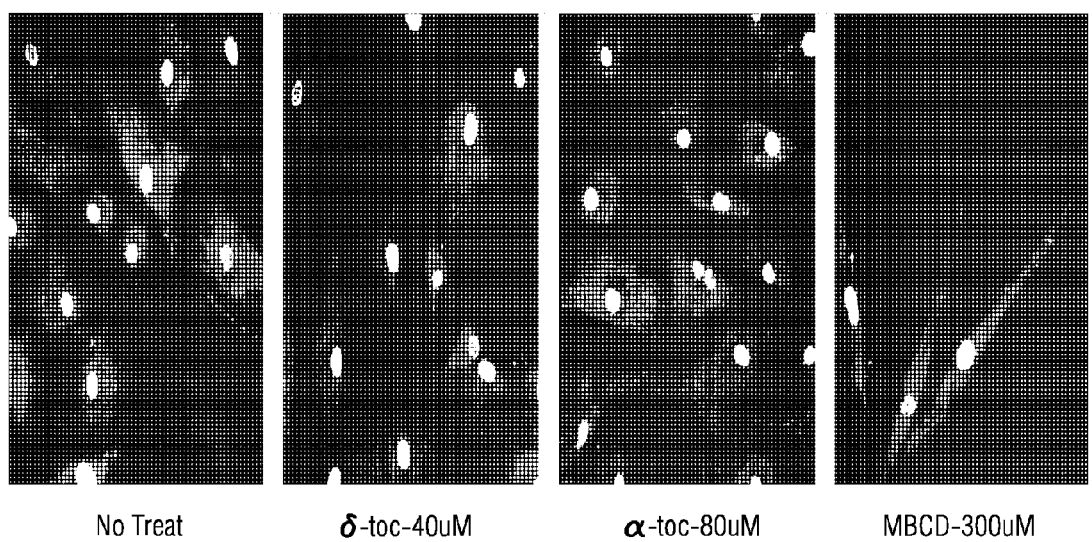
Figure 18:
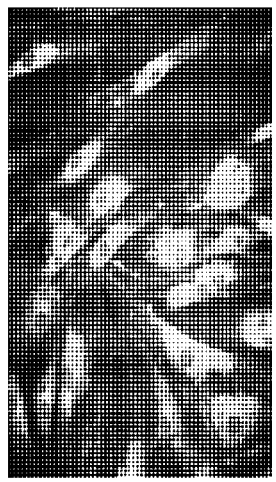
FIG. 18. Control WT cells treated with 80 uM alpha-tocopherol and 40 uM delta-tocopherol for four days. Top panel with red emission is for total lipids including the polar lipids such as phospholipids. Bottom panel is with emission for non-polar lipids including cholesteryl ester and triglycerides.
Figure 18:
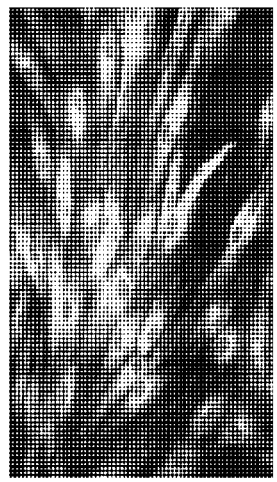
Figure 18:
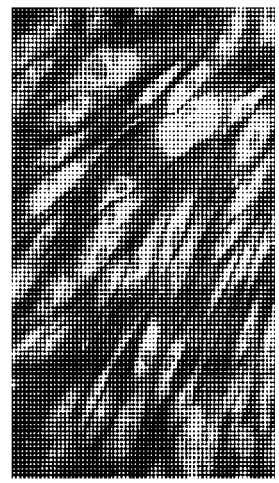
Figure 18:
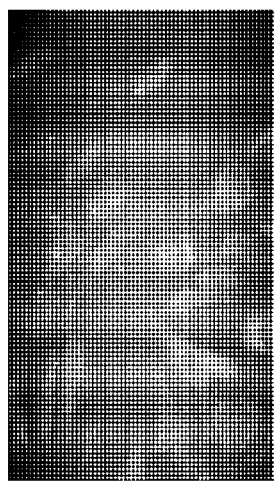
Figure 18:
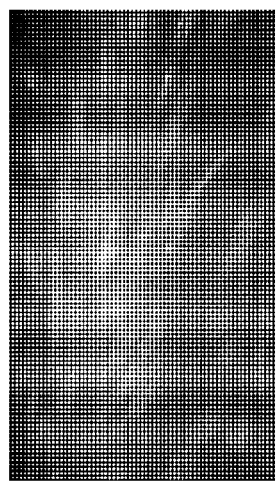
Figure 18:
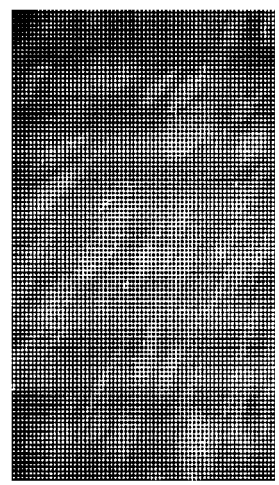
Figure 19:
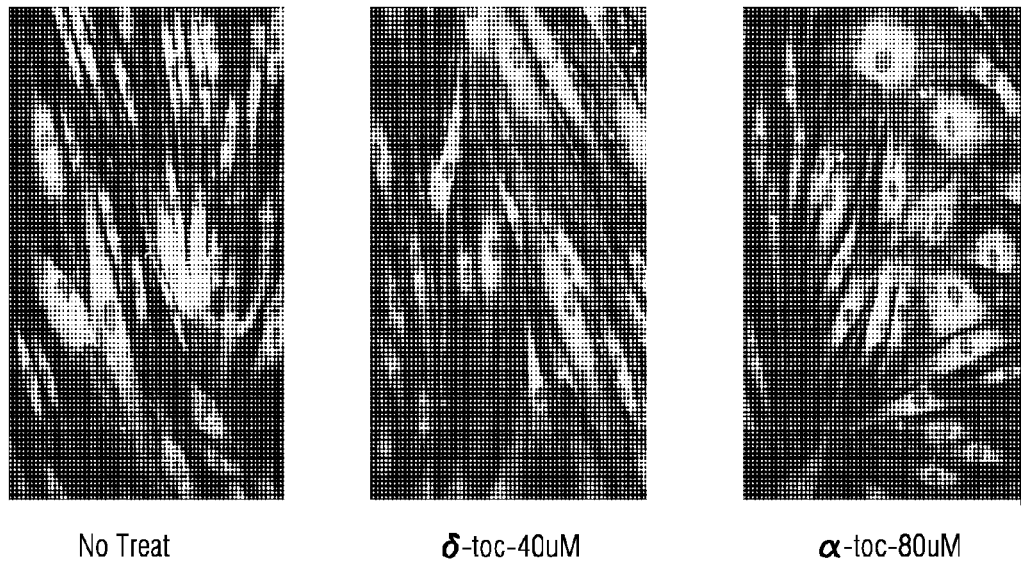
FIG. 19. Images of Nile red staining in Farber disease cells treated with 80 uM alpha-tocopherol and 40 uM delta-tocopherol for four days. Top panel with red emission is for total lipids including the polar lipids such as phospholipids. Bottom panel is with emission for non-polar lipids including cholesteryl ester and triglycerides.
Figure 19:
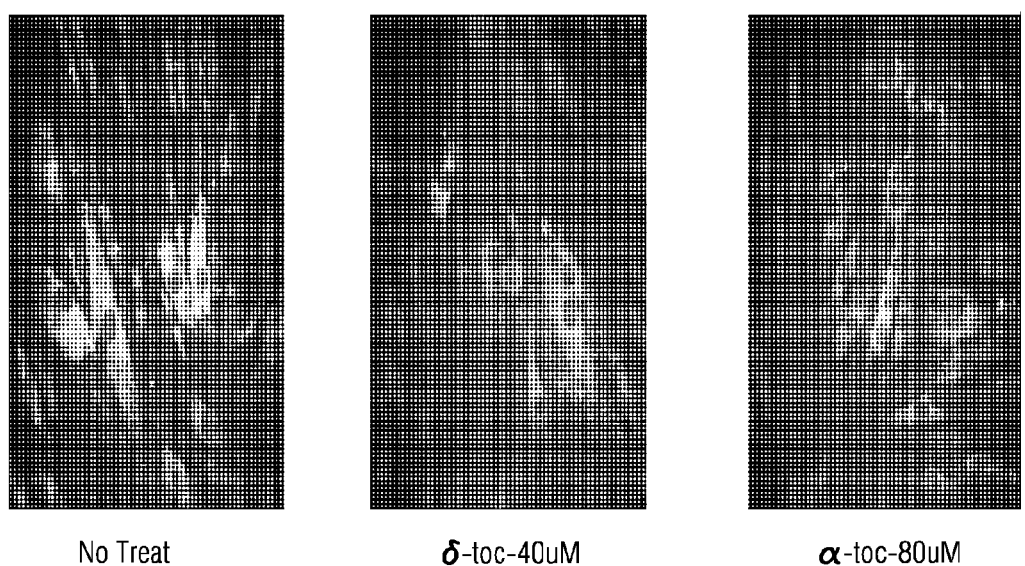
Figure 20:
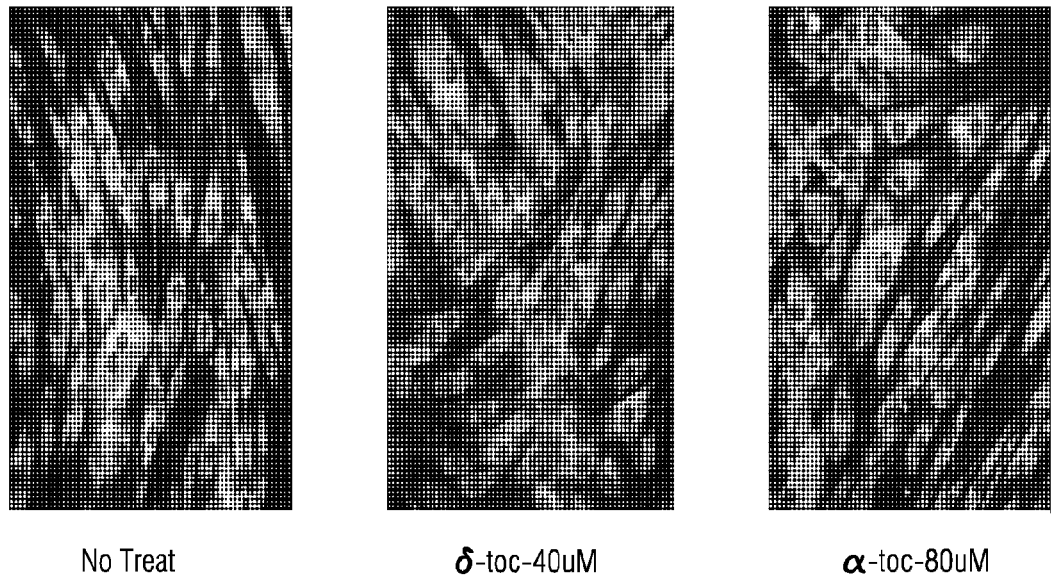
FIG. 20. Images of Nile red staining in NPA disease cells treated with 80 uM alpha-tocopherol and 40 uM delta-tocopherol for four days. Top panel with red emission is for total lipids including the polar lipids such as phospholipids. Bottom panel is with emission for non-polar lipids including cholesteryl ester and triglycerides.
Figure 20:
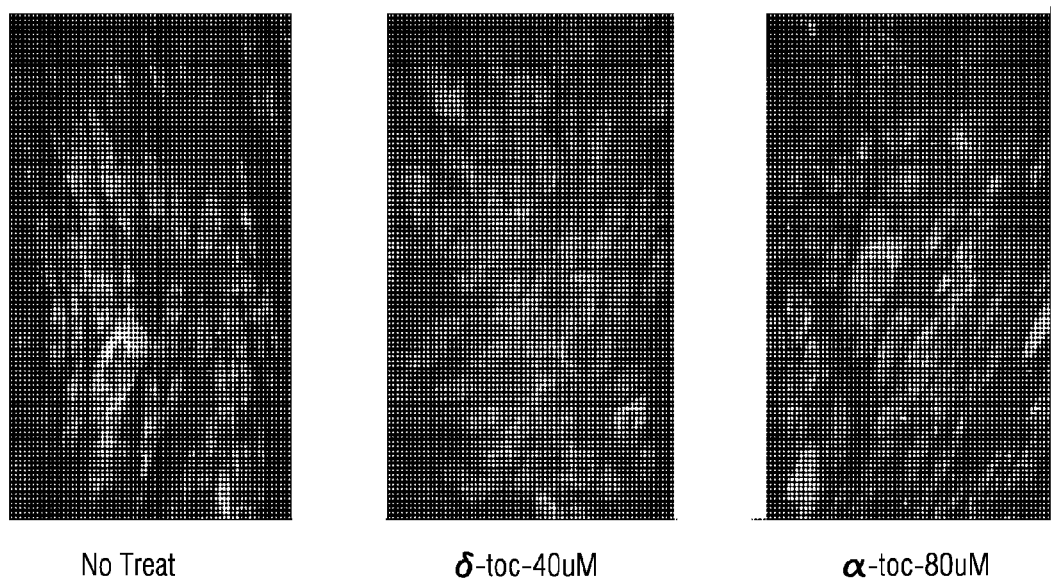
Figure 21:
FIG. 21. Images of Nile red staining in Wolman6144 disease cells (from one patient) treated with 80 uM alpha-tocopherol and 40 uM delta-tocopherol for four days. Top panel with red emission is for total lipids including the polar lipids such as phospholipids. Bottom panel is with emission for non-polar lipids including cholesteryl ester and triglycerides.
Figure 21:
Figure 21:
Figure 21:
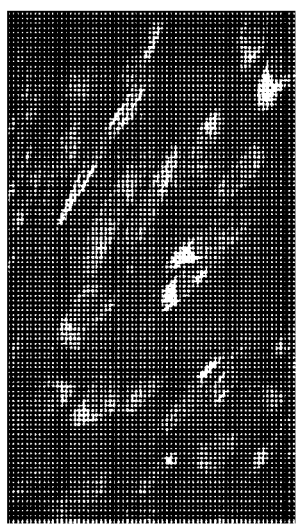
Figure 21:
Figure 21:
Figure 22:
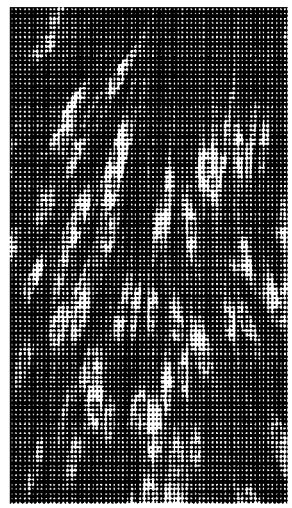
FIG. 22. Images of Nile red staining in Wolman11851 disease cells (from one patient) treated with 80 uM alpha-tocopherol and 40 uM delta-tocopherol for four days. Top panel with red emission is for total lipids including the polar lipids such as phospholipids. Bottom panel is with emission for non-polar lipids including cholesteryl ester and triglycerides.
Figure 22:
Figure 22:
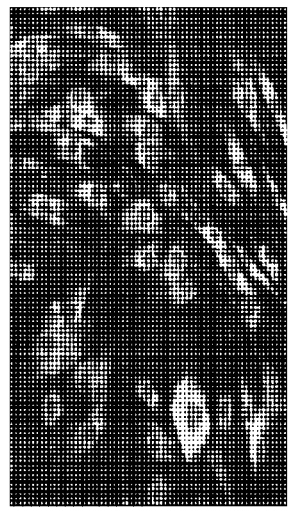
Figure 22:
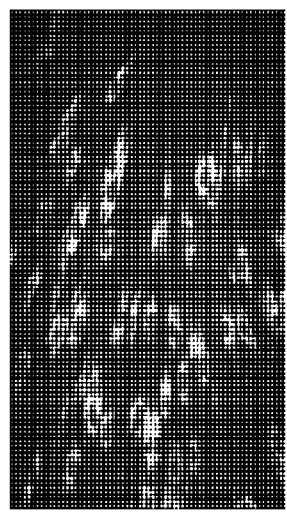
Figure 22:
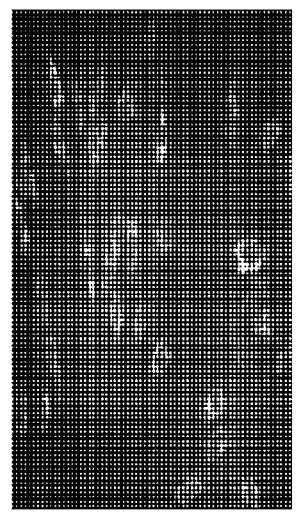
Figure 22:
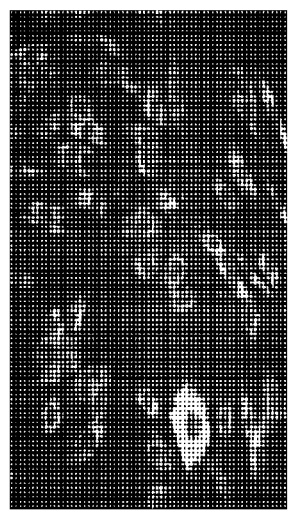
Figure 23:
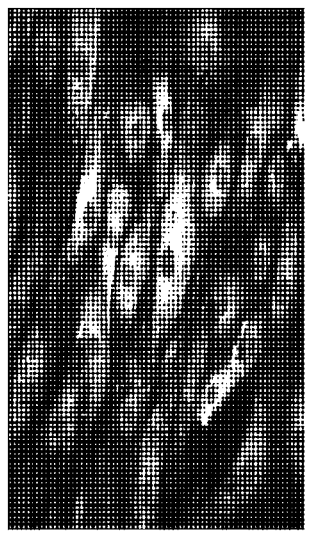
FIG. 23. Images of Nile red staining in Tay Sachs disease cells treated with 80 uM alpha-tocopherol and 40 uM delta-tocopherol for four days. Top panel with red emission is for total lipids including the polar lipids such as phospholipids. Bottom panel is with emission for non-polar lipids including cholesteryl ester and triglycerides.
Figure 23:
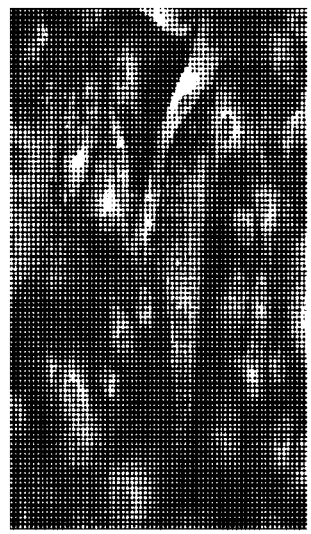
Figure 23:
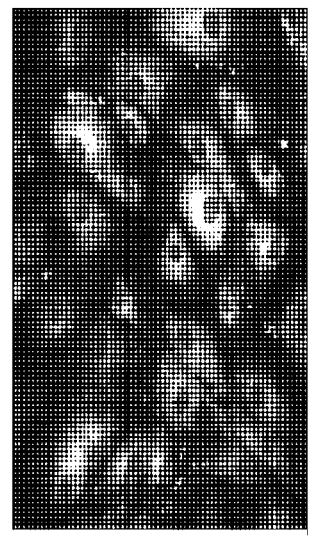
Figure 23:
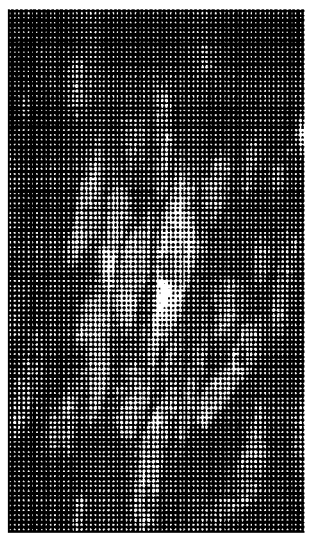
Figure 23:
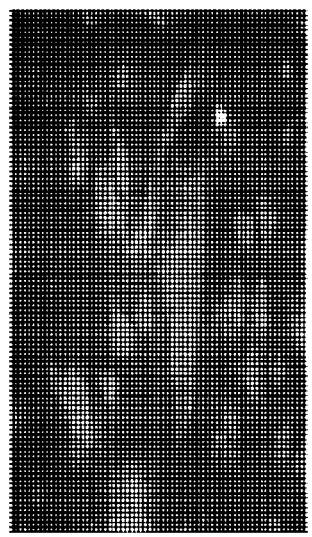
Figure 23:
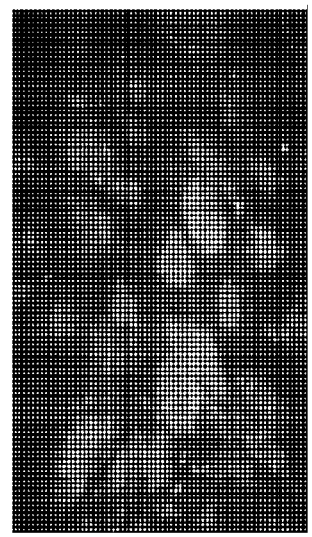
Figure 24:
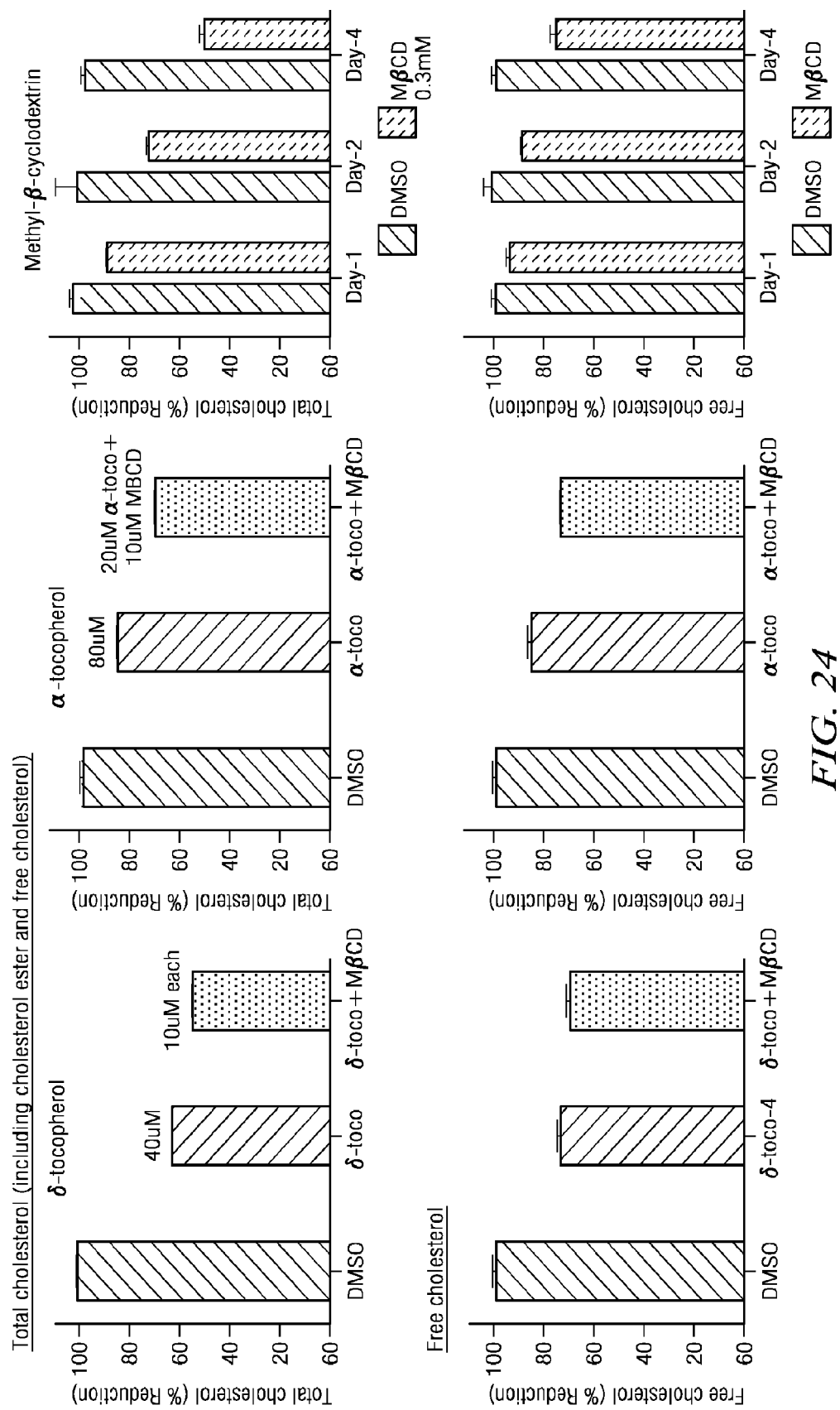
FIG. 24. Combination therapy of vitamin E and cyclodextrin. In Wolman disease cells, the combination sub-effective concentrations of alpha-tocopherol (20 uM) or delta-tocopherol (10 uM) with 10 uM MBCD (methyl-beta-cyclodextrin) showed cholesterol reduction effect as the sole therapy with 40 uM delta-tocopherol and 80 uM alpha-tocopherol. MBCD at 0.3 mM showed the time dependent reduction on cholesterol level in these cells. These results indicated the synergetic or additive effect for delta-tocopherol and clyclodextrin for the treatment of lysosomal storage diseases. This drug combination therapy has advantages including reduced dosages for both drugs (to reduce potential adverse effects) and enhanced therapeutic effect (because two drugs have different mechanism of action).

The lethality of NPCD is primarily caused by the neuronal degeneration though the cholesterol accumulation is observed in many cell types. We show the cholesterol reduction effect of δ-tocopherol is present in human NPC neuronal cells, using the neuron-like cells differentiated from the mesenchymal stem cells (MSC) derived that were obtained from two NPCD patients. Both the NPCD patient derived MSC cell lines showed the similar cholesterol accumulation as that in the NPCD fibroblasts. The phenotype of cholesterol accumulation was preserved in these neuron-like cells after the differentiation as well as in the MSC cells (FIG. 5a). A set of neuronal markers were used to examine both wild type and NPCD cells after the differentiation including including GAD65 (glutamic acid decarboxylase), galactocerebroside, neurofilament M, NeuN (neuronal nuclear antigen) and neuron-specific beta III tubulin. We show that only neuron-specific beta III tubulin was positive in both cells after neuronal differentiation whereas none of matured markers were found, indicating that these cells were neuron-like cells but not matured neurons. In addition, only a small portion of cells were differentiated similarly between wild type and mutant cells. δ-tocopherol treatment showed significant reduction in cholesterol accumulation as well as a decrease in lysosome size in these neuron-like NPCD cells that were co-localized by the filipin staining with a neuronal marker (FIG. 5b). δ-tocopherol effects on the reduction of accumulated free cholesterol and decrease in lysosome size in late endosomes and lysosomes exist in the neuron-like NPCD cells and the NPCD MSC cells, as it was observed in the NPCD fibroblasts.

The gene expression pattern of NPCD cells after the treatment with δ-tocopherol is disclosed in comparison with the wild type fibroblasts. (Table 1)

Among the genes identified in Table 1, the expressions of LDLR and ABCA1 genes significantly reduced in NPC cells after the δ-tocopherol treatment. NPC1 mutant cells were noted for an upregulation of (1) cholesterol homeostasis (transport) genes, (2) genes involved in membrane trafficking, (3) genes associated with calcium regulation, (4) genes involved in oxidative stress and (5) genes associated with Alzheimer's disease.

NPCD patient-derived fibroblasts have an altered expression of many genes that regulate lipid and cholesterol homeostasis, including those that affect lipid and protein transport, and de novo synthesis of saturated lipids and cholesterol (Table 1).

In the NPCD fibroblasts, LDLR and ABCA1 were upregulated inducing more transport of cholesterol into the cell. The upregulation of LDLR in NPC cells is not the result of reduced available free cholesterols in cells although they are accumulated in late endosomes and lysosomes. ABCA1 transport was reported as one of cholesterol efflux mechanisms. It may also transport cholesterols into cells dependent on the balance of cholesterols in and out of cells. The treatment with δ-tocopherol in NPCD cells decreased expression of these two genes. In addition, the expression of several lipid and cholesterol synthetic genes, such as SCD and HMGCR, were also decreased after the δ-tocopherol treatment in NPCD cells which may be due to a direct interaction with or decreased expression of sterol sensors in the cell like SREBPs and INSIG1, reflecting an overall reduction in endoplasmic reticulum stress.

Beta-cyclodextrin (cyclo) has been reported to reduce cholesterol accumulation in NPC mouse and cat models as well as increase in life span in these models. Cyclodextrin is also a pharmaceutical excipient that is used for formulation of hydrophobic drugs. The mechanism of action for cyclo to treat NPC is still unclear. It has been implicated that the cyclo induced endocytosis and/or exocytosis may contribute to its effect on the cholesterol reduction in NPC cells and animal models. However, high concentration (0.3 to 10 mM in vitro) and large dose (4 g/Kg body weight) are need for the effect of cyclo on the NPC that may cause the side and toxic effects. We disclose the combination therapy of δ-tocopherol and cyclodextrin in reduced concentrations.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

EXAMPLES

The following example is provided for illustrative purposes only and is not intended to limit the scope of the invention.

Example 1

Human skin fibroblast cell lines GM5657, GM56599 and GM3123 were purchased from the Coriell Cell Repository (Caden, N.J.). Other human skin fibroblast cell lines NPC19, NPC20, and NPC25 were established by Forbes D. Porter. Cell growth media (DMEM), L-glutamine, FBS, penicillin/streptomycin, Hoechst and LysoTracker Red were purchased from Invitrogen (Carlsbad, Calif.). Filipin, gamma-tocopherol (T1782, >96% purity) were obtained from Sigma-Aldrich (St. Louis, Mo.). Delta-tocopherol was purchased from Sigma-Aldrich and purified to 99% by AAA using a protocol co-developed by AAA and NCGC. Alpha-(cat#100008377), gamma-(cat#10008494), delta-(cat#10008513) tocotrienols were obtained from Cayman Chemical (Ann Arbor, Mich.) in ethanol solutions. They were lyophilized and dissolved in DMSO. Beta-tocopherol (99% purity, cat #ASB-00020319-050) was purchased from ChromaDex (Irvine, Calif.).

The primary human skin fibroblasts were cultured in DMEM media (Invitrogen, cat#11995-040) supplemented with 10% FBS, 100 unit/ml penicillin and 100 ug/ml streptomycin in a humidified incubator (5% CO2) at 37° C.

The adipose mesenchymal stem cells (HMSC.AD-100, HMSC-NPC22 and HMSC-NPC23) were isolated from two NPC patients as well as one heath individual and provided by Celleng-tech (Coralville, Iowa). These cells were maintained in MSC expansion media (Celleng-tech, cat#HMSC.E.Media-450) supplemented with 10% FBS 100 unit/ml penicillin and 100 ug/ml streptomycin at 5% $CO_2$, 37° C. For neural differentiation, cells were initially plated at 30% confluency (~2500 cells/cm$^2$) using MSC expansion media. After 24 hours, MSC expansion media were withdrew. Cells were washed twice with Dulbecco's phosphate Buffer saline (invitrogen) and incubated with neural differentiation media (Celleng-tech, cat#NEU.D.Media-450) supplemented with 10% FBS, 100 unit/ml penicillin and 100 ug/ml streptomycin at 5% $CO_2$, 37° C. for additional 3 days.

A collection of 2,800 compounds enriched in approved drugs were set up internally at NIH Chemical Genomics Center and dissolved in DMSO solution as 10 mM stock solution. The compounds were serially diluted at 1:2.236 ratio in DMSO in 384-well plates to yield fifteen concentrations and then formatted into 1,536-well plates at 5 μl/well as the compound source plates. The concentrations of diluted compounds in the source plates ranged from 0.28 μM to 10 mM. In the screen experiments, 23 nl of compounds in DMSO solution was transferred to assay plates containing 5 ul/well cell culture medium. The final concentrations of compounds in the screening assay plates ranged from 1.32 nM to 46 μM.

The free cholesterol level in these cells was then measured by a cholesterol oxidase coupled HRP/amplex red detection method with a commercial available kit (Invitrogen). The cells were seeded to black, tissue culture-treated 1536-well plates (Greiner Bio-One, Monroe, N.C.) at 800 cells/well in 5 μl medium by a Multidrop Combi dispenser (Thermo Scientific, Waltham, Mass.) and cultured for 24 hours. The assay plates were added with 23 nl/well of compound DMSO solution using a pintool station (Kalypsys, San Diego, Calif.) and cultured for 3 days. The 1536-well assay plate was washed by a plate-inverted centrifugation method that removing medium by centrifuging plates upside down against a stack of paper towel at 1000 rpm for 1 min followed by addition of 7 ul/well PBS buffer, repeating for two times. The PBS buffer was added with a 45 degree angled dispenser (Kalypsys) or a Multi-Drop Combi dispenser set at medium speed to reduce disturbance to the cells. After the cell wash, 2.5 ul/well of detection mixture from the kit was added followed by 1 hour incubation at 37° C. With the addition of the detection mixture, the cells were lysed by the detergent containing buffer and free cholesterols in cell lysate were oxidized by cholesterol oxidase to produce $H_2O_2$ which reacting with amplex red dye in the presence of horseradish peroxidase to yield red fluorescence signal. A ViewLux plate reader (PerkinElmer, Boston, Mass.) was used to measure the fluorescent signal in assay plates with the excitation of 573 nm and emissions of 610 nm.

Filipin dye staining was used to determine the level of free cholesterol accumulation in cells (27, 28). Cells were seeded at 1000 cells/well in 100 ul medium in the black/clear bottom, tissue culture treated 96-well plates (Greiner Bio-One, Monroe, N.C.) for culture overnight or in a designated time. The cells were washed twice with the HBBS buffer and fixed with 100 ul/well 3.2% formaldehyde at room temperature for 30 minutes. After three times of plate wash with PBS buffer, cells were stained with 50 ug/ml filipin, which was freshly-dissolved in DMSO at 10 mg/ml and then diluted in PBS buffer. Samples were then washed twice with PBS buffer and stored in 4° C. On the day of imaging, cells were stained with 2 uM of CellMask Red (Invitrogen, H32711) in PBS at room temperature for 1 h. Samples were viewed and photographed using a Nikon Eclipse Ti microscope with a 20× objective equipped with CCD camera. DAPI filter and TRITC filter were used to visualize filipin and CellMask Red, respectively. The images were processed by Adobe Photoshop.

Lysotracker is fluorescent dye that stains acidic compartments in live cells and is well-retained after aldehyde fixation. We have optimized a lysotracker staining assay to visualize the enlarged lysosome size in the NPC skin fibroblasts by applying appropriate concentration of lysotracker dye in comparison with these normal fibroblast cells. Cells were seeded at 8000 cells/well in 100 ul medium in a black/clear bottom, tissue culture treated plate and cultured overnight or in a dedicated time. The cells were live-stained with 100 u/well 50 nM Lysotracker Red-99 dye (Invitrogen) dissolved medium at 37° C. for 1 hr followed by two-times plate wash with PBS buffer using the plate-inverted centrifugation method. The plate was then added with 100 ul/well 3.2% formaldehyde and 1 ug/ml Hoechst 33342 (Invitrogen) in PBS and incubated at room temperature for 30 minutes. After three times of plate wash with PBS buffer, samples were stored at 4° C. until imaging. Samples were photographed using an IN Cell Analyzer 1000 (GE Healthcare) with a 20× objective equipped with CCD camera. DAPI filter and TRITC filter were used to visualize Hoechst and Lysotracker red, respectively. The images were processed by Adobe Photoshop.

To measure the cytotoxicity of compounds, an ATP content assay was used with a commercial assay kit (ATP-Lite, PerkinElmer). Cells were seeded in white solid 1536-well plates and treated with compounds same as in the cholesterol oxidase assay describe above. After 3-day compound treatment, 3 ul/well detection mixture (prepared according to the manufacturer's instructions) was added to each well and the plates were incubated for 10 min at room temperature followed by a measurement using a Viewlux plate reader in a luminescence mode. The buffer in the detection mixture lyses cells and releases cellular ATP which reacts with luciferin in the presence of luciferase to produce light. The luminescence signal reduces if the cells are killed by the compound during the 3-day treatment.

Cell pellets were collected from 100-mm dishes and washed once with 10 ml PBS. Proteins were assayed using the BCA kit (Sigma-Aldrich) and lipids were extracted by modified Bligh and Dyer procedure (29) from the cells. Internal standards were added based on protein concentration that included N12:0 sphingomyelin, D7-cholesterol, 17:0 cholesterol ester (Avanti Polar Lipids, Inc). A portion of the lipid extract was used for detection of sphingomyelins using direct infusion mass spectrometric assay with lithium hydroxide for facilitating ionization and the rest was used to convert cholesterol and its ester into acetate by derivatization. The derivatization was performed by treating the dried crude lipid extract with solutions of 1M acetic acid with 1M DMAP in chloroform and 1M EDC in chloroform at 50° C. for 2 hours. The derivatized product was extracted with hexane and analyzed by direct infusion mass spectrometric assay with 5% ammonium hydroxide for facilitating ionization.

A triple-quadrupole mass spectrometer equipped with an electrospray was used for analysis of lipids in positive mode. Sphingomyelins, cholesterol and cholesterol esters were detected by neutral loss scan of 213 (collision energy: 50 V), neutral loss scan of 77 (collision energy: 14 V) and precursor ion scan of m/z 369 (collision energy: 14 V) respectively. Data processing of mass spectrometric analyses including ion peak selection, data transferring, peak intensity comparison and quantitation was conducted using self-programmed Microsoft Excel macros (30).

MSC cells were seeded on coverslips on day 0 in MSC expansion medium. On day 1, cells were washed twice with warm PBS buffer and then incubated with MSC neuronal differentiation medium. On day 4, media were replaced with fresh neuronal differentiation medium. On day 6, cells were fixed with 3.2% paraformaldehyde in HBSS for 15 min. Immunocytochemistry for neuronal beta III tubulin and unesterified cholesterol (filipin staining) was performed as described. The coverslips were examined y a XXX microscope. The following filter sets were used: for filipin, excitation 360/40 nM, emission filter 460/50 nM.

Five NPC fibroblast cell lines as well as five normal fibroblast cell lines were treated with 40 μM delta-tocopherol for 5 days with a medium change and sully of fresh compound on $3^{rd}$ day. The total RNAs was prepared as the standard method described previously 0. The microarray gene expression experiment was carried out in a core microarray facility at NHGRI with a set of AAAAA chips (Affymetrix).

Partek Genomics Software Suite (Copyright, Partek Inc.) was used to perform analysis of microarray data. Affymetrix cel files were loaded into the software using the RMA algorithm, which involved background correction, quantile normalization, log-2 transformation, and median polish summarization. PCA and hierarchical clustering identified one sample as an outlier. This sample (sample number 12) was not considered for further analysis.

ANOVA was performed to identify the differentially expressed genes for three comparisons: 1) NPC_DMSO vs WT_DMSO 2) NPC_tocopheol-treated vs NPC_DMSO-treated and 3) WT_tocopherol-treated vs WT_DMSO-treated. An FDR cut-off of 0.05 failed to identify any genes with differential expression. So, a p-value cut-off of 0.01 was applied with an aim to validate the true positives using RT-PCR.

Cell lysates were prepared as previously described (31) and proteins in lysates were quantified using Bicinchoninic Acid (BCA) Protein Assay Kit (Sigma-Aldrich). Samples were heated at 65 C for 10 min before resolved by SDS-PAGE under reducing conditions. Proteins were transferred to PVDF membranes (Bio-Rad Laboratory) using either Criterion Blotter (Bio-Rad Laboratory) or iBlot dry blotting devices (Invitrogen). For NPC1 and HMG-CoA reductase detection, rabbit polyclonal antibodies against NPC1 (Abcam, cat #ab36983, 1:2000) or HMG-CoA reductase (Millipore, cat #07-457, 1:1000) were used, respectively. A peroxidase-conjugated donkey anti-rabbit IgG (Santa Cruz) was used as secondary antibody at a 1:500 dilution.

The compound library screen data was analyzed using software developed internally at NIH Chemical Genomics Center (32). Concentration-response curves analyzed and EC50/IC50s were calculated with the Prism® software (GraphPad, San Diego, Calif.).

Example 2

Patient derived primary skin fibroblasts have been used as disease models for testing the effect of alpha- and delta-tocopherols. Fibroblasts from patients with Farber disease, Niemann Pick Type A diease, Wolman diseases and Say Tachs disease were obtained from Coriell Cell repository (Camden, N.J.) that accumulating ceramide, sphingomyelin, cholesteryl ester and GM2 gangliosides in ysosomes, respectively.

(1) Amplex-red cholesterol assay. This biochemical assay (Invitrogen) uses cholesterol oxidase and a HRP-Amplex-re reporting system to measure the free cholesterol level in cells. With the addition of acid lipase to this assay, that hydrolyzes cholesterol ester to free cholesterol, the level of total cholesterol in cells including the cholesterol ester can be measured. This assay was used for detecting the total cholesterol level of in fibroblasts from patients with Wolman disease.

(2) Lysotracker dye (Invitrogen) staining assay. Lysotracker dye stains the acidic compartment in cells. We use an optimal concentration of lysotracker dye that shows the enlarged lysosomes due to the storage of lipids in fibroblasts from patients with lysosomal storage diseases including Farber, Wolman, Say tachs and Niemann Pick Type A diseases. Drug treatment can reduce the size of the enlarged lysosome as the lipid storage is decreased.

(3) Nile-red dye staining assay. Nile red dye (Invitrogen) stains two groups of lipids. At excitation1=460-480 nm and emission1=535 nm, it stains the non-polar lipids such as cholesterol ester and triglycerides. At excitation2=500-540 nm and emission2 590-615 nm it stains the total lipids including the polar lipids such as phospholipids.

(4). Intracellular calcium assay. We used a fluorescence calcium dye (Fluo-8, AAT Bioquest, CA) to measure the transit increase of intracellular calcium stimulated by alpha-tocopherol and delta-tocopherol. Cytosal calcium increase is a second messenger which mediates a variety of cellular functions including exocytosis.

δ-tocopherol has significant effect on reduction of enlarged lysosome size and storage of macromolecules in patient derived fibroblasts of five lysosmal storage diseases. The mechanism of action for δ-tocopherol is direct insertion into the lipid membrane in cells that facilitates lipid movement in membrane and discharge of accumulated lysosomal macromolecules out of cells. Thus, δ-tocopherol can be used to treat all types of lysosomal storage diseases. We teach the combination therapy using vitamin E and cyclodextrin has synergetic or additive effect that can reduce dosage and adverse effect as well as increase the efficacy due to different mechanism of action for two drugs.

Example 3

It is envisioned that δ-tocopherol will be used either alone or in combination with inhibitors of CYP4F2 for the treatment of lysosomal storage disorders. Purified Delta-tocopherol purified to pharmacologically acceptable levels for the treatment of humans would be performed. Dosage curves would be examined for both cytotoxicity and efficacy, as would be understood by one with skill in the art. Patients could have multiple dose treatments, for multiple days, depending on efficacy, toxicity and half life with regard to delta tocopherol.

TABLE 1

Genes differentially expressed in NPC fibroblasts, or with tocopherol treatment

| Gene | Class | NPC vs WT untreated | Toco treat NPC | Toco treat WT |
| --- | --- | --- | --- | --- |
| LDLR | Cholesterol trafficking | 1.3 | −2.0 | −2.0 |
| ABCA1 | Cholesterol trafficking | 1.3 | −2.0 | −1.4 |
| CPE | Intracellular transport | 2.7 | NC | NC |
| SCD | Lipid and cholesterol synthesis | 2.1 | −3.9 | −3.5 |
| FADS2 | Lipid and cholesterol synthesis | 1.2 | −2.5 | −2.0 |

TABLE 1-continued

Genes differentially expressed in NPC fibroblasts, or with tocopherol treatment

| Gene | Class | NPC vs WT untreated | Toco treat NPC | Toco treat WT |
|---|---|---|---|---|
| ACACA | Lipid and cholesterol synthesis | 1.1 | −1.5 | −1.5 |
| HMGCR | Lipid and cholesterol synthesis | 1.8 | −1.7 | −1.5 |
| HMGCS1 | Lipid and cholesterol synthesis | 1.6 | −1.9 | −1.6 |
| SC4MOL | Lipid and cholesterol synthesis | 2.3 | −1.4 | −1.7 |
| DHCR7 | Lipid and cholesterol synthesis | 1.3 | −1.7 | −1.6 |
| INSIG1 | Cholesterol homeostasis | 1.6 | −1.8 | −1.6 |
| SREBF1 | Cholesterol homeostasis | −1.1 | −1.4 | −1.2 |
| SREBF2 | Cholesterol homeostasis | 1.1 | −1.6 | −1.6 |
| MMP1 | Inflammation | 4.9 | 2.7 | 5.0 |
| MMP3 | Inflammation | 5.1 | 1.7 | 2.0 |
| TNFAIP6 | Inflammation | 2.9 | NC | NC |
| FRRS1 | Ferric Iron reductase | 2.9 | 1.1 | −1.1 |
| NOX4 | Generation of ROS | 2.7 | −1.1 | −1.7 |

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

What is claimed is:

1. A method for treating lysosomal storage disorder comprising administering to a subject in need thereof a pharmaceutically effective composition comprising δ tocopherol, wherein the composition does not comprise α tocopherol.

2. The method of claim 1, wherein the lysosomal storage disorder is selected from the group consisting of Niemann-Pick Type C disease, Niemann-Pick Type A disease, Wolman disease, Farber disease, and Tay Sachs disease.

3. The method of claim 2, wherein the lysosomal storage disorder is Niemann-Pick Type C Disease.

4. The method of claim 1, wherein the composition further comprises cyclodextrin.

5. The method of claim 1, wherein the composition is administered in a dosage resulting in a plasma concentration of δ tocopherol of 10 µM to 50 µM.

6. The method of claim 1, wherein the composition is administered in a dosage of less than 1000 IU/kg per day of δ tocopherol.

7. The method of claim 1, wherein a route of administering is selected from the group consisting of oral, topical, suppository, intravenous, intradermic, intragaster, intramuscular, and intraperitoneal administration.

8. A method for reducing cholesterol accumulation in cells comprising administering to a host in need thereof an effective amount of a composition comprising δ tocopherol, wherein the composition does not contain a tocopherol.

9. The method of claim 8, wherein a route of administering is selected from the group consisting of oral, topical, suppository, intravenous, intradermic, intragaster, intramuscular, and intraperitoneal administration.

10. The method of claim 8, wherein the composition is administered in a dosage resulting in a plasma concentration of δ tocopherol of 10 µM to 50 µM.

11. The method of claim 8, wherein the composition is administered in a dosage of less than 1000 IU/kg per day of δ tocopherol.

12. The method of claim 8, wherein the cholesterol accumulation is free cholesterol.

13. The method of claim 8, wherein the cholesterol accumulation is in lysosomes of the cells.

14. The method of claim 8, wherein the host is human.

15. The method of claim 1, wherein the composition comprises at least one inhibitor of CYP4F2.

16. The method of claim 15, wherein the inhibitor is selected from the group consisting of ketoconazole, sesame seeds, lignan sesamin, and lignan sesaminol.

17. The method of claim 8, wherein the composition further comprises cyclodextrin.

18. The method of claim 17, wherein the cyclodextrin is 2-hydroxypropyl-beta-cyclodextrin.

* * * * *